(12) United States Patent
Vesto et al.

(10) Patent No.: US 11,087,878 B2
(45) Date of Patent: Aug. 10, 2021

(54) METHODS AND SYSTEMS FOR IMPROVING CONNECTIONS WITHIN A HEALTHCARE ECOSYSTEM

(71) Applicant: General Electric Company, Schenectady, NY (US)

(72) Inventors: Guy Robert Vesto, Barrington, IL (US); Rizwan Ahmed, Bangalore (IN)

(73) Assignee: General Electric Company, Schenectady, NY (US)

( * ) Notice: Subject to any disclaimer, the term of this patent is extended or adjusted under 35 U.S.C. 154(b) by 368 days.

(21) Appl. No.: 16/269,070

(22) Filed: Feb. 6, 2019

(65) Prior Publication Data
US 2019/0172590 A1   Jun. 6, 2019

Related U.S. Application Data

(63) Continuation of application No. 14/840,998, filed on Aug. 31, 2015, now Pat. No. 10,216,902.
(Continued)

(51) Int. Cl.
G16H 40/67 (2018.01)
G16H 50/70 (2018.01)
G16H 50/50 (2018.01)

(52) U.S. Cl.
CPC ............ *G16H 40/67* (2018.01); *G16H 50/50* (2018.01); *G16H 50/70* (2018.01)

(58) Field of Classification Search
CPC ........ G06F 19/324; G06F 19/00; G16H 50/70
See application file for complete search history.

(56) References Cited

U.S. PATENT DOCUMENTS

2003/0028852 A1   2/2003  Thurman
2003/0216938 A1  11/2003  Shour
(Continued)

FOREIGN PATENT DOCUMENTS

CN   1268006 A   9/2000

OTHER PUBLICATIONS

United States Patent and Trademark Office, "Notice of Allowance," issued in connection with U.S. Appl. No. 14/840,998, dated Oct. 12, 2018, 22 pages.
(Continued)

*Primary Examiner* — Linh Giang Le
(74) *Attorney, Agent, or Firm* — Hanley, Flight & Zimmerman, LLC

(57) ABSTRACT

A systems, method, and apparatus to improve connections within a healthcare ecosystem are provided. Example systems, methods, and apparatus can facilitate dynamic interface definition and configuration. An example method includes storing a plurality of reusable interface and route definitions to translate and exchange data messages between source and target systems in a healthcare ecosystem; monitoring message exchanges and message patterns in the healthcare environment via a machine learning system to predict traffic and utilization patterns in the healthcare ecosystem; tracking metadata regarding connections involving the source and target systems and storing the metadata in a graph database; suggesting connections between the source and target systems based on the monitored message exchanges and message patterns and metadata from the graph database using graph analytics; provisioning an interface between the source and target systems based on a suggested connection, the interface provisioned from the reusable interface and route definitions based on the suggested connection.

20 Claims, 24 Drawing Sheets

Related U.S. Application Data

(60) Provisional application No. 62/044,271, filed on Aug. 31, 2014.

(56) References Cited

U.S. PATENT DOCUMENTS

| | | |
|---|---|---|
| 2008/0046292 A1 | 2/2008 | Myers et al. |
| 2009/0080408 A1 | 3/2009 | Natoli et al. |
| 2009/0240526 A1 | 9/2009 | Vesto et al. |
| 2011/0077973 A1 | 3/2011 | Breitenstein et al. |
| 2011/0119088 A1 | 5/2011 | Gunn |
| 2016/0063191 A1 | 3/2016 | Vesto et al. |

OTHER PUBLICATIONS

CN application 201510545659.X filed Aug. 31, 2015—Second Office Action dated Oct. 10, 2020; 15 pages.
CN1268006A—English translation of abstract; Espacenet.com Jan. 14, 2021; 1 page.

METHODS AND SYSTEMS FOR IMPROVING CONNECTIONS WITHIN A HEALTHCARE ECOSYSTEM

RELATED APPLICATIONS

This patent claims priority as a continuation to U.S. Non-Provisional patent application Ser. No. 14/840,998, entitled "METHODS AND SYSTEMS FOR IMPROVING CONNECTIONS WITHIN A HEALTHCARE ECOSYSTEM," filed on Aug. 31, 2015, which claims priority to U.S. Provisional Application Ser. No. 62/044,271, entitled "METHODS AND SYSTEMS FOR IMPROVING CONNECTIONS WITHIN A HEALTHCARE ECOSYSTEM," which was filed on Aug. 31, 2014, each of which is hereby incorporated herein by reference in its entirety.

FIELD OF DISCLOSURE

The present disclosure relates to a healthcare interface as a service, and more particularly to systems, methods and computer program products to facilitate improved connection between components of a healthcare ecosystem via an interface as a service.

BACKGROUND

The statements in this section merely provide background information related to the disclosure and may not constitute prior art.

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored can include patient medication orders, medical histories, imaging data, test results, diagnosis information, management information, and/or scheduling information, for example.

BRIEF SUMMARY

In view of the above, systems, methods, and computer program products which improve connections within a healthcare ecosystem are provided. Example systems, methods, and apparatus can facilitate dynamic interface definition and configuration. The above-mentioned needs are addressed by the subject matter described herein and will be understood in the following specification.

This summary briefly describes aspects of the subject matter described below in the Detailed Description, and is not intended to be used to limit the scope of the subject matter described in the present disclosure.

Certain examples provide a method to facilitate dynamic interface definition and configuration via an integration platform. The example method includes storing, using a particularly configured processor, a plurality of reusable interface and route definitions to translate and exchange data messages between source and target systems in a healthcare ecosystem. The example method includes monitoring, using the processor, message exchanges and message patterns in the healthcare environment via a machine learning system to predict traffic and utilization patterns in the healthcare ecosystem. The example method includes tracking, using the processor, metadata regarding connections involving the source and target systems and storing the metadata in a graph database. The example method includes suggesting, using the processor, connections between the source and target systems based on the monitored message exchanges and message patterns and metadata from the graph database using graph analytics. The example method includes provisioning, using the processor, an interface between the source system and the target system based on a suggested connection, the interface provisioned from the plurality of reusable interface and route definitions based on the suggested connection.

Certain examples provide a computer storage medium including program instructions for execution by a particularly configured computing device to perform a method to improve connections within a healthcare ecosystem.

Certain examples provide a method to facilitate dynamic interface definition and configuration via an integration platform. The example method includes storing a plurality of reusable interface and route definitions to translate and exchange data messages between source and target systems in a healthcare ecosystem. The example method includes monitoring message exchanges and message patterns in the healthcare environment via a machine learning system to predict traffic and utilization patterns in the healthcare ecosystem. The example method includes tracking metadata regarding connections involving the source and target systems and storing the metadata in a graph database. The example method includes suggesting connections between the source and target systems based on the monitored message exchanges and message patterns and metadata from the graph database using graph analytics. The example method includes provisioning an interface between the source system and the target system based on a suggested connection, the interface provisioned from the plurality of reusable interface and route definitions based on the suggested connection.

Certain examples provide an integration platform system to facilitate dynamic interface definition and configuration. The example integration platform system includes a particularly configured processor. The example processor is particularly configured to at least store a plurality of reusable interface and route definitions to translate and exchange data messages between source and target systems in a healthcare ecosystem. The example processor is particularly configured to at least monitor message exchanges and message patterns in the healthcare environment via a machine learning system to predict traffic and utilization patterns in the healthcare ecosystem. The example processor is particularly configured to at least track metadata regarding connections involving the source and target systems and storing the metadata in a graph database. The example processor is particularly configured to at least suggest connections between the source and target systems based on the monitored message exchanges and message patterns and metadata from the graph database using graph analytics. The example processor is particularly configured to at least provision an interface between the source system and the target system based on a suggested connection, the interface provisioned from the plurality of reusable interface and route definitions based on the suggested connection.

BRIEF DESCRIPTION OF THE DRAWINGS

The features and technical aspects of the system and method disclosed herein will become apparent in the fol

DETAILED DESCRIPTION

Figure 1:
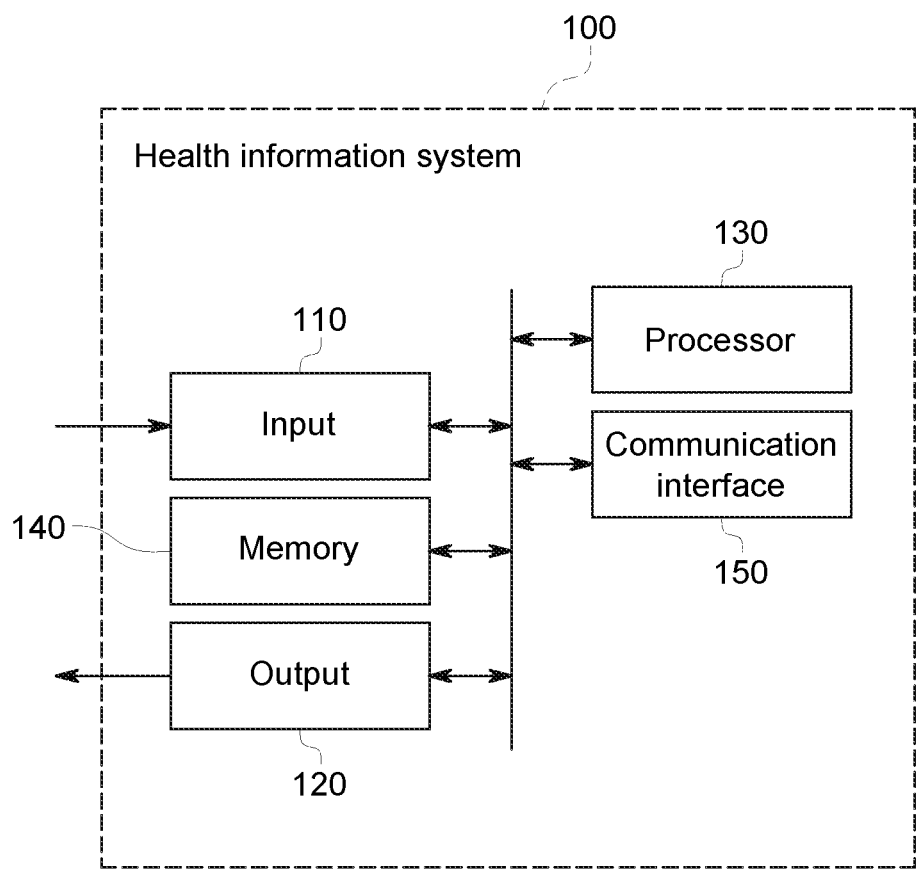
- FIG. 1 shows a block diagram of an example healthcare-focused information system.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

I. Overview

Aspects disclosed and described herein enable an end-to-end system design of an intelligent cloud-based integration platform for healthcare data exchanges between information technology (IT) systems in a healthcare ecosystem or environment. Aspects provide connectivity between source systems deployed within healthcare facilities such as hospitals, ambulatory and/or specialty practices clinics, etc., that are to be able to exchange healthcare relevant clinical and/or non-clinical information with target systems. A target system includes one or more business partner systems, such as health information exchanges (HIEs), payers, labs, workforce and referral agencies, specialized diagnostics labs, DNA sequencing labs, disease registries, federal agencies, etc., that can send back a meaningful response which the source system can embed into its business processing logic and/or workflow. Certain aspects provide intelligent mediation via a routing engine and analytics to drive and continuously improve connections within a healthcare ecosystem or environment. Certain aspects also facilitate a novel and flexible method of interface provisioning with easy configuration and deployment to allow for new target systems to be integrated in a "plug-and-play" manner. Interface implementations support healthcare standard protocols such as Health-Level Seven (HL7) v2.x/3.x, HL7 FHIR, Digital Imaging and Communications in Medicine (DICOM), Clinical Document Architecture (CDA)/Consolidated CDA (CCDA), and Integrating the Healthcare Enterprise's (IHE's) Cross-Enterprise Document Sharing (XDS), Patient Identifier Cross-Referencing/Patient Demographics Query (PIX/PDQ), Laboratory (LAB), Audit Trail and Node Authentication (ATNA), and other IHE profiles.

Certain aspects attempt to continuously improve connectivity within a healthcare ecosystem/environment by optimizing/improving on cost, time to implementation and patient outcome. Certain aspects provide a cloud-based integration platform that facilitates reuse and rapid provision of new endpoints, interfaces and routes within the healthcare ecosystem/environment. To meet this goal, there are number of challenges to overcome: 1.) Privacy compliance—maintaining data sharing agreements between players within a dynamic ecosystem. 2.) Business model shift—making integration and connectivity a commodity and focusing on value added services 3.) Technical challenges—how to integrate disparate systems where there is a high degree of variability in the HL7 standard 4.) Automation—how to eliminate the manual and labor intensive integration work required today 5.) Pragmatism and focus—how to keep the focus on the key objective of improving patient outcome without boiling the ocean 6.) How to virally drive adoption.

In certain examples, value added services are enabled through a connected application ecosystem, which helps make healthcare connectivity a ubiquitous commodity. Certain examples help facilitate interoperability, which has been one of the healthcare industry's biggest problems for years. A lack of interoperability has led to a tremendous amount of redundancy and inefficiency in integration solutions, which is overcome by the presently described technology.

Certain examples remove overlap and redundancy in approach within various healthcare products in solving interoperability problems using a consistent solution across common healthcare integration scenarios. In certain examples, the consistent solution includes providing multiple individual standalone pluggable interfaces as a facade to healthcare IT products inter-connected by a centralized intelligent platform that performs relevant interactions and orchestration.

In certain examples, new interfaces are created and provisioned using a standardized governance model and through automation. Certain examples build a graph of the connected healthcare ecosystem/environment to enable connections to be improved or optimized and traffic roadblocks to be avoided. Certain examples facilitate an agile, flexible, adaptable, "plug-and-play" integration strategy.

In certain examples, deploying a tele-ICU (intensive care unit) as an Interface-as-a-Service (IaaS) to help enable care providers at a remote hospital to provide advanced consultation, care and monitoring to critically ill patients without having to transfer them to super-specialty hospitals. Remote ICU monitoring technology through the tele-ICU allows an intensivist at the command center to monitor real-time parameters of critically ill patients from remote ICUs/ Hospitals on a 24/7 basis. This technology model (using concepts around Interfacing-as-a-Service as its central thesis) has ramifications in products that can be launched in the tele-Radiology or the tele-ER space.

While other cloud-based healthcare integration solutions use commodity HL7 integration engines in "the cloud" to address specific healthcare integration or connectivity problems, certain aspects differentiate, at least in part, by focusing on connecting and continuously improving the connections within the healthcare ecosystem/environment while at the same time driving down cost of integration and improving patient outcome. Certain aspects employ a combination of business model innovations (e.g., freemium, predictive analytics, partnering, social networking, standardization, process efficiency, added value, process automation and simplification, etc.), technical innovation (e.g., architecture and design choices that support the types of business model innovations mentioned, etc.) and analytics (e.g., graph analytics plus machine learning to discover patterns, etc.).

Other aspects, such as those discussed in the following and others as can be appreciated by one having ordinary skill in the art upon reading the enclosed description, are also possible.

II. Example Operating Environment

Health information, also referred to as healthcare information and/or healthcare data, relates to information generated and/or used by a healthcare entity. Health information can be information associated with health of one or more patients, for example. Health information can include protected health information (PHI), as outlined in the Health Insurance Portability and Accountability Act (HIPAA), which is identifiable as associated with a particular patient and is protected from unauthorized disclosure. Health information can be organized as internal information and external information. Internal information includes patient encounter information (e.g., patient-specific data, aggregate data, comparative data, etc.) and general healthcare operations information, etc. External information includes comparative data, expert and/or knowledge-based data, etc. Information can have both a clinical (e.g., diagnosis, treatment, prevention, etc.) and administrative (e.g., scheduling, billing, management, etc.) purpose.

Institutions, such as healthcare institutions, having complex network support environments and sometimes chaotically driven process flows utilize secure handling and safeguarding of the flow of sensitive information (e.g., personal privacy). A need for secure handling and safeguarding of information increases as a demand for flexibility, volume, and speed of exchange of such information grows. For example, healthcare institutions provide enhanced control and safeguarding of the exchange and storage of sensitive patient PHI and employee information between diverse locations to improve hospital operational efficiency in an operational environment typically having a chaotic-driven demand by patients for hospital services. In certain examples, patient identifying information can be masked or even stripped from certain data depending upon where the data is stored and who has access to that data. In some examples, PHI that has been "de-identified" can be re-identified based on a key and/or other encoder/decoder.

A healthcare information technology infrastructure can be adapted to service multiple business interests while providing clinical information and services. Such an infrastructure can include a centralized capability including, for example, a data repository, reporting, discreet data exchange/connectivity, "smart" algorithms, personalization/consumer decision support, etc. This centralized capability provides information and functionality to a plurality of users including medical devices, electronic records, access portals, pay for performance (P4P), chronic disease models, and clinical health information exchange/regional health information organization (HIE/RHIO), and/or enterprise pharmaceutical studies, home health, for example.

Interconnection of multiple data sources helps enable an engagement of all relevant members of a patient's care team and helps improve an administrative and management burden on the patient for managing his or her care. Particularly, interconnecting the patient's electronic medical record and/ or other medical data can help improve patient care and management of patient information. Furthermore, patient care compliance is facilitated by providing tools that automatically adapt to the specific and changing health conditions of the patient and provide comprehensive education and compliance tools to drive positive health outcomes.

In certain examples, healthcare information can be distributed among multiple applications using a variety of database and storage technologies and data formats. To provide a common interface and access to data residing across these applications, a connectivity framework (CF) can be provided which leverages common data and service models (CDM and CSM) and service oriented technologies, such as an enterprise service bus (ESB) to provide access to the data.

In certain examples, a variety of user interface frameworks and technologies can be used to build applications for health information systems including, but not limited to, MICROSOFT® ASP.NET, AJAX®, MICROSOFT® Windows Presentation Foundation, GOOGLE® Web Toolkit, MICROSOFT® Silverlight, ADOBE®, and others. Applications can be composed from libraries of information widgets to display multi-content and multi-media information, for example. In addition, the framework enables users to tailor layout of applications and interact with underlying data.

In certain examples, an advanced Service-Oriented Architecture (SOA) with a modern technology stack helps provide robust interoperability, reliability, and performance. The example SOA includes a three-fold interoperability strategy including a central repository (e.g., a central repository built from Health Level Seven (HL7) transactions), services for working in federated environments, and visual integration with third-party applications. Certain examples provide portable content enabling plug 'n play content exchange among healthcare organizations. A standardized vocabulary using common standards (e.g., LOINC, SNOMED CT, RxNorm, FDB, ICD-9, ICD-10, etc.) is used for interoperability, for example. Certain examples provide an intuitive user interface to help minimize end-user training. Certain examples facilitate user-initiated launching of third-party applications directly from a desktop interface to help provide a seamless workflow by sharing user, patient, and/or other contexts. Certain examples provide real-time (or at least substantially real time assuming some system delay) patient data from one or more information technology (IT) systems and facilitate comparison(s) against evidence-based best practices. Certain examples provide one or more dashboards for specific sets of patients. Dashboard(s) can be based on condition, role, and/or other criteria to indicate variation(s) from a desired practice, for example.

a. Example Healthcare Information System

An information system can be defined as an arrangement of information/data, processes, and information technology that interact to collect, process, store, and provide informational output to support delivery of healthcare to one or more patients. Information technology includes computer technology (e.g., hardware and software) along with data and telecommunications technology (e.g., data, image, and/or voice network, etc.).

Turning now to the figures, FIG. 1 shows a block diagram of an example healthcare-focused information system 100. The example system 100 can be configured to implement a variety of systems and processes including image storage (e.g., picture archiving and communication system (PACS), etc.), image processing and/or analysis, radiology reporting and/or review (e.g., radiology information system (RIS), etc.), computerized provider order entry (CPOE) system, clinical decision support, patient monitoring, population health management (e.g., population health management system (PHMS), health information exchange (HIE), etc.), healthcare data analytics, cloud-based image sharing, electronic medical record (e.g., electronic medical record system (EMR), electronic health record system (EHR), electronic patient record (EPR), personal health record system (PHR), etc.), and/or other health information system (e.g., clinical information system (CIS), hospital information system (HIS), patient data management system (PDMS), laboratory information system (LIS), cardiovascular information system (CVIS), etc.

As illustrated in FIG. 1, the example information system 100 includes an input 110, an output 120, a processor 130, a memory 140, and a communication interface 150. The components of the example system 100 can be integrated in one device or distributed over two or more devices.

The example input 110 can include a keyboard, a touchscreen, a mouse, a trackball, a track pad, optical barcode recognition, voice command, etc. or combination thereof used to communicate an instruction or data to the system 100. The example input 110 can include an interface between systems, between user(s) and the system 100, etc.

The example output 120 can provide a display generated by the processor 130 for visual illustration on a monitor or the like. The display can be in the form of a network interface or graphic user interface (GUI) to exchange data, instructions, or illustrations on a computing device via the communication interface 150, for example. The example output 120 can include a monitor (e.g., liquid crystal display (LCD), plasma display, cathode ray tube (CRT), etc.), light emitting diodes (LEDs), a touch-screen, a printer, a speaker, or other conventional display device or combination thereof.

The example processor 130 includes hardware and/or software configuring the hardware to execute one or more tasks and/or implement a particular system configuration. The example processor 130 processes data received at the input 110 and generates a result that can be provided to one or more of the output 120, memory 140, and communication interface 150. For example, the example processor 130 can take user annotation provided via the input 110 with respect to an image displayed via the output 120 and can generate a report associated with the image based on the annotation. As another example, the processor 130 can process updated patient information obtained via the input 110 to provide an updated patient record to an EMR via the communication interface 150.

The example memory 140 can include a relational database, an object-oriented database, a data dictionary, a clinical data repository, a data warehouse, a data mart, a vendor neutral archive, an enterprise archive, etc. The example memory 140 stores images, patient data, best practices, clinical knowledge, analytics, reports, etc. The example memory 140 can store data and/or instructions for access by the processor 130. In certain examples, the memory 140 can be accessible by an external system via the communication interface 150.

In certain examples, the memory 140 stores and controls access to encrypted information, such as patient records, encrypted update-transactions for patient medical records, including usage history, etc. In an example, medical records can be stored without using logic structures specific to medical records. In such a manner the memory 140 is not searchable. For example, a patient's data can be encrypted with a unique patient-owned key at the source of the data. The data is then uploaded to the memory 140. The memory 140 does not process or store unencrypted data thus minimizing privacy concerns. The patient's data can be downloaded and decrypted locally with the encryption key.

For example, the memory 140 can be structured according to provider, patient, patient/provider association, and document. Provider information can include, for example, an identifier, a name, and address, a public key, and one or more security categories. Patient information can include, for example, an identifier, a password hash, and an encrypted email address. Patient/provider association information can include a provider identifier, a patient identifier, an encrypted key, and one or more override security categories. Document information can include an identifier, a patient identifier, a clinic identifier, a security category, and encrypted data, for example.

The example communication interface 150 facilitates transmission of electronic data within and/or among one or more systems. Communication via the communication interface 150 can be implemented using one or more protocols. In some examples, communication via the communication interface 150 occurs according to one or more standards (e.g., Digital Imaging and Communications in Medicine (DICOM), Health Level Seven (HL7), ANSI X12N, etc.). The example communication interface 150 can be a wired interface (e.g., a data bus, a Universal Serial Bus (USB) connection, etc.) and/or a wireless interface (e.g., radio frequency, infrared, near field communication (NFC), etc.). For example, the communication interface 150 can communicate via wired local area network (LAN), wireless LAN, wide area network (WAN), etc. using any past, present, or future communication protocol (e.g., BLUETOOTH™, USB 2.0, USB 3.0, etc.).

In certain examples, a Web-based portal may be used to facilitate access to information, patient care and/or practice management, etc. Information and/or functionality available via the Web-based portal may include one or more of order entry, laboratory test results review system, patient information, clinical decision support, medication management, scheduling, electronic mail and/or messaging, medical resources, etc. In certain examples, a browser-based interface can serve as a zero footprint, zero download, and/or other universal viewer for a client device.

In certain examples, the Web-based portal serves as a central interface to access information and applications, for example. Data may be viewed through the Web-based portal or viewer, for example. Additionally, data may be manipulated and propagated using the Web-based portal, for example. Data may be generated, modified, stored and/or used and then communicated to another application or system to be modified, stored and/or used, for example, via the Web-based portal, for example.

The Web-based portal may be accessible locally (e.g., in an office) and/or remotely (e.g., via the Internet and/or other private network or connection), for example. The Web-based portal may be configured to help or guide a user in accessing data and/or functions to facilitate patient care and practice management, for example. In certain examples, the Web-based portal may be configured according to certain rules, preferences and/or functions, for example. For example, a user may customize the Web portal according to particular desires, preferences and/or requirements.

b. Example Healthcare Infrastructure

Figure 2:
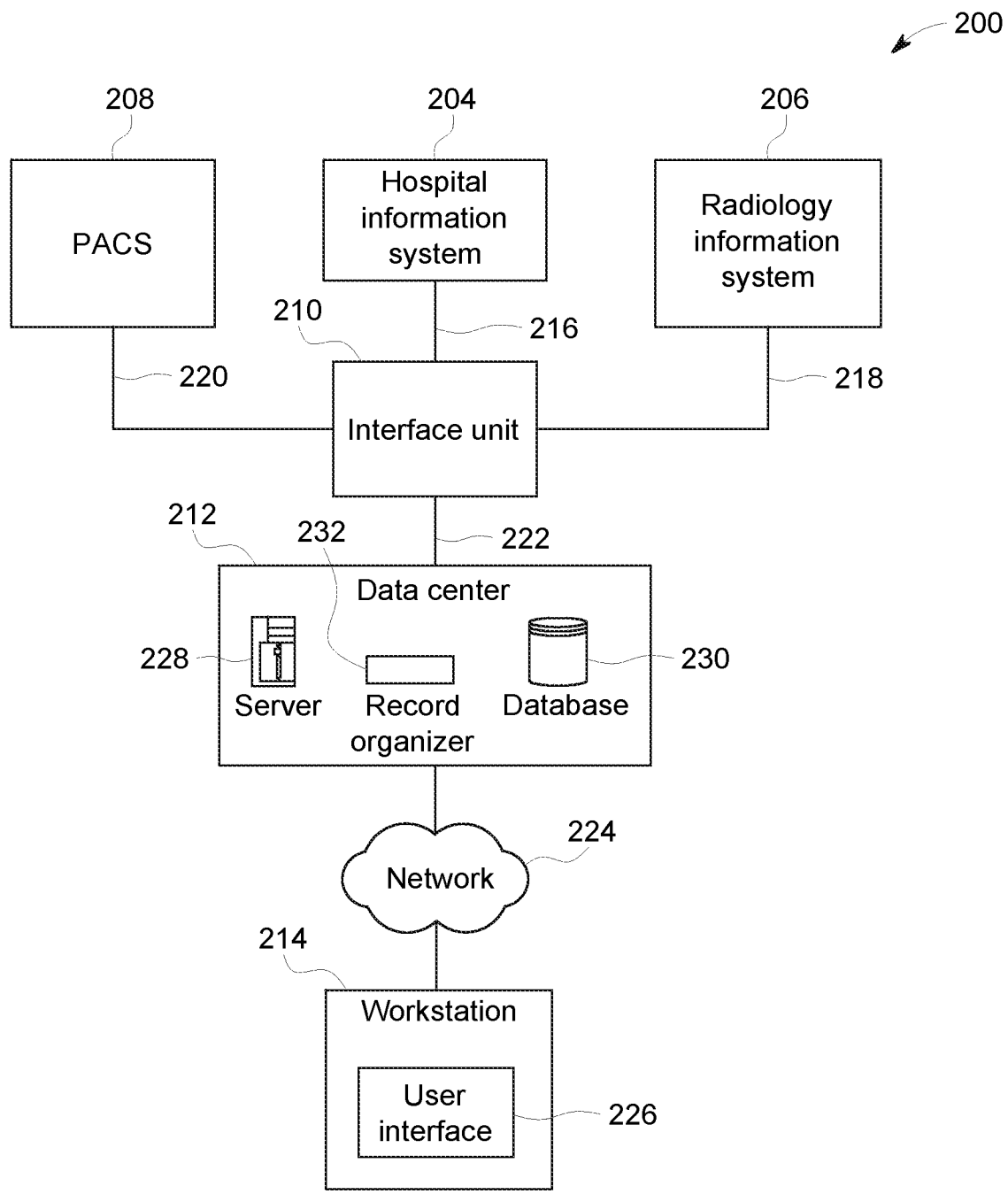
FIG. 2 shows a block diagram of an example healthcare information infrastructure including one or more systems.

FIG. 2 shows a block diagram of an example healthcare information infrastructure 200 including one or more subsystems such as the example healthcare-related information system 100 illustrated in FIG. 1. The example healthcare system 200 includes a HIS 204, a RIS 206, a PACS 208, an interface unit 210, a data center 212, and a workstation 214. In the illustrated example, the HIS 204, the RIS 206, and the PACS 208 are housed in a healthcare facility and locally archived. However, in other implementations, the HIS 204, the RIS 206, and/or the PACS 208 can be housed one or more other suitable locations. In certain implementations, one or more of the PACS 208, RIS 206, HIS 204, etc., can be implemented remotely via a thin client and/or downloadable software solution. Furthermore, one or more components of the healthcare system 200 can be combined and/or implemented together. For example, the RIS 206 and/or the PACS 208 can be integrated with the HIS 204; the PACS 208 can be integrated with the RIS 206; and/or the three example information systems 204, 206, and/or 208 can be integrated together. In other example implementations, the healthcare system 200 includes a subset of the illustrated information systems 204, 206, and/or 208. For example, the healthcare system 200 can include only one or two of the HIS 204, the RIS 206, and/or the PACS 208. Information (e.g., scheduling, test results, exam image data, observations, diagnosis, etc.) can be entered into the HIS 204, the RIS 206, and/or the PACS 208 by healthcare practitioners (e.g., radiologists, physicians, and/or technicians) and/or administrators before and/or after patient examination.

The HIS 204 stores medical information such as clinical reports, patient information, and/or administrative information received from, for example, personnel at a hospital, clinic, and/or a physician's office (e.g., an EMR, EHR, PHR, etc.). The RIS 206 stores information such as, for example, radiology reports, radiology exam image data, messages, warnings, alerts, patient scheduling information, patient demographic data, patient tracking information, and/or physician and patient status monitors. Additionally, the RIS 206 enables exam order entry (e.g., ordering an x-ray of a patient) and image and film tracking (e.g., tracking identities of one or more people that have checked out a film). In some examples, information in the RIS 206 is formatted according to the HL-7 (Health Level Seven) clinical communication protocol. In certain examples, a medical exam distributor is located in the RIS 206 to facilitate distribution of radiology exams to a radiologist workload for review and management of the exam distribution by, for example, an administrator.

The PACS 208 stores medical images (e.g., x-rays, scans, three-dimensional renderings, etc.) as, for example, digital images in a database or registry. In some examples, the medical images are stored in the PACS 208 using the Digital Imaging and Communications in Medicine (DICOM) format. Images are stored in the PACS 208 by healthcare practitioners (e.g., imaging technicians, physicians, radiologists) after a medical imaging of a patient and/or are automatically transmitted from medical imaging devices to the PACS 208 for storage. In some examples, the PACS 208 can also include a display device and/or viewing workstation to enable a healthcare practitioner or provider to communicate with the PACS 208.

The interface unit 210 includes a hospital information system interface connection 216, a radiology information system interface connection 218, a PACS interface connection 220, and a data center interface connection 222. The interface unit 210 facilities communication among the HIS 204, the RIS 206, the PACS 208, and/or the data center 212. The interface connections 216, 218, 220, and 222 can be implemented by, for example, a Wide Area Network (WAN) such as a private network or the Internet. Accordingly, the interface unit 210 includes one or more communication components such as, for example, an Ethernet device, an asynchronous transfer mode (ATM) device, an 802.11 device, a DSL modem, a cable modem, a cellular modem, etc. In turn, the data center 212 communicates with the workstation 214, via a network 224, implemented at a plurality of locations (e.g., a hospital, clinic, doctor's office, other medical office, or terminal, etc.). The network 224 is implemented by, for example, the Internet, an intranet, a private network, a wired or wireless Local Area Network, and/or a wired or wireless Wide Area Network. In some examples, the interface unit 210 also includes a broker (e.g., a Mitra Imaging's PACS Broker) to allow medical information and medical images to be transmitted together and stored together.

The interface unit 210 receives images, medical reports, administrative information, exam workload distribution information, and/or other clinical information from the information systems 204, 206, 208 via the interface connections 216, 218, 220. If necessary (e.g., when different formats of the received information are incompatible), the interface unit 210 translates or reformats (e.g., into Structured Query Language ("SQL") or standard text) the medical information, such as medical reports, to be properly stored at the data center 212. The reformatted medical information can be transmitted using a transmission protocol to enable different medical information to share common identification elements, such as a patient name or social security number. Next, the interface unit 210 transmits the medical information to the data center 212 via the data center interface connection 222. Finally, medical information is stored in the data center 212 in, for example, the DICOM format, which enables medical images and corresponding medical information to be transmitted and stored together.

The medical information is later viewable and easily retrievable at the workstation 214 (e.g., by their common identification element, such as a patient name or record number). The workstation 214 can be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. The workstation 214 receives commands and/or other input from a user via, for example, a keyboard, mouse, track ball, microphone, etc. The workstation 214 is capable of implementing a user interface 226 to enable a healthcare practitioner and/or administrator to interact with the healthcare system 200. For example, in response to a request from a physician, the user interface 226 presents a patient medical history. In other examples, a radiologist is able to retrieve and manage a workload of exams distributed for review to the radiologist via the user interface 226. In further examples, an administrator reviews radiologist workloads, exam allocation, and/or operational statistics associated with the distribution of exams via the user interface 226. In some examples, the administrator adjusts one or more settings or outcomes via the user interface 226.

The example data center 212 of FIG. 2 is an archive to store information such as images, data, medical reports, and/or, more generally, patient medical records. In addition, the data center 212 can also serve as a central conduit to information located at other sources such as, for example, local archives, hospital information systems/radiology information systems (e.g., the HIS 204 and/or the RIS 206), or medical imaging/storage systems (e.g., the PACS 208 and/or connected imaging modalities). That is, the data center 212 can store links or indicators (e.g., identification numbers, patient names, or record numbers) to information. In the illustrated example, the data center 212 is managed by an application server provider (ASP) and is located in a centralized location that can be accessed by a plurality of systems and facilities (e.g., hospitals, clinics, doctor's offices, other medical offices, and/or terminals). In some examples, the data center 212 can be spatially distant from the HIS 204, the RIS 206, and/or the PACS 208 (e.g., at GENERAL ELECTRIC® headquarters).

The example data center 212 of FIG. 2 includes a server 228, a database 230, and a record organizer 232. The server 228 receives, processes, and conveys information to and from the components of the healthcare system 200. The database 230 stores the medical information described herein and provides access thereto. The example record organizer 232 of FIG. 2 manages patient medical histories, for example. The record organizer 232 can also assist in procedure scheduling, for example.

Certain examples can be implemented as cloud-based clinical information systems and associated methods of use. An example cloud-based clinical information system enables healthcare entities (e.g., patients, clinicians, sites, groups, communities, and/or other entities) to share information via web-based applications, cloud storage and cloud services. For example, the cloud-based clinical information system may enable a first clinician to securely upload information into the cloud-based clinical information system to allow a second clinician to view and/or download the information via a web application. Thus, for example, the first clinician may upload an x-ray image into the cloud-based clinical information system, and the second clinician may view the x-ray image via a web browser and/or download the x-ray image onto a local information system employed by the second clinician.

In certain examples, users (e.g., a patient and/or care provider) can access functionality provided by the system 200 via a software-as-a-service (SaaS) implementation over a cloud or other computer network, for example. In certain examples, all or part of the system 200 can also be provided via platform as a service (PaaS), infrastructure as a service (IaaS), etc. For example, the system 200 can be implemented as a cloud-delivered Mobile Computing Integration Platform as a Service. A set of consumer-facing Web-based, mobile, and/or other applications enable users to interact with the PaaS, for example.

c. Industrial Internet Examples

The Internet of things (also referred to as the "Industrial Internet") relates to an interconnection between a device that can use an Internet connection to talk with other devices on the network. Using the connection, devices can communicate to trigger events/actions (e.g., changing temperature, turning on/off, provide a status, etc.). In certain examples, machines can be merged with "big data" to improve efficiency and operations, provide improved data mining, facilitate better operation, etc.

Big data can refer to a collection of data so large and complex that it becomes difficult to process using traditional data processing tools/methods. Challenges associated with a large data set include data capture, sorting, storage, search, transfer, analysis, and visualization. A trend toward larger data sets is due at least in part to additional information derivable from analysis of a single large set of data, rather than analysis of a plurality of separate, smaller data sets. By analyzing a single large data set, correlations can be found in the data, and data quality can be evaluated.

Figure 3:
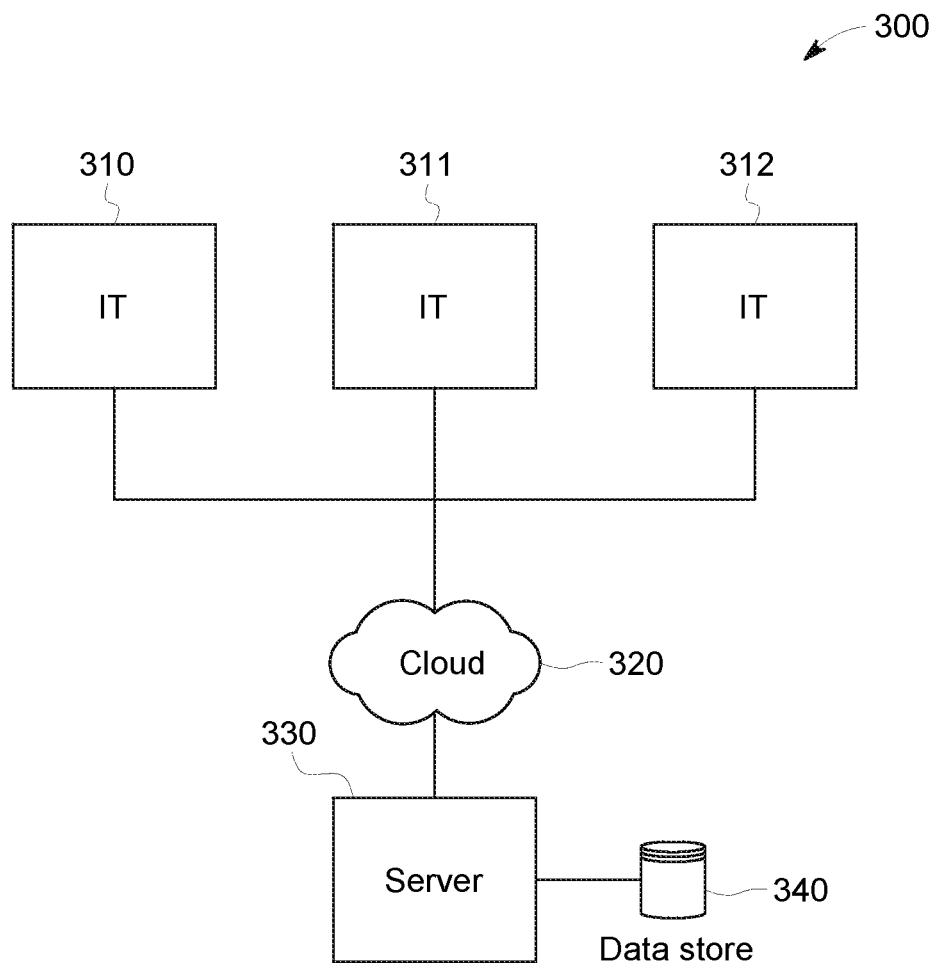
FIG. 3 shows an example industrial internet configuration including a plurality of health-focused systems.

FIG. 3 illustrates an example industrial internet configuration 300. The example configuration 300 includes a plurality of health-focused systems 310-312, such as a plurality of health information systems 100 (e.g., PACS, RIS, EMR, etc.) communicating via the industrial internet infrastructure 300. The example industrial internet 300 includes a plurality of health-related information systems 310-312 communicating via a cloud 320 with a server 330 and associated data store 340.

As shown in the example of FIG. 3, a plurality of devices (e.g., information systems, imaging modalities, etc.) 310-312 can access a cloud 320, which connects the devices 310-312 with a server 330 and associated data store 340. Information systems, for example, include communication interfaces to exchange information with server 330 and data store 340 via the cloud 320. Other devices, such as medical imaging scanners, patient monitors, etc., can be outfitted with sensors and communication interfaces to enable them to communicate with each other and with the server 330 via the cloud 320.

Thus, machines 310-312 in the system 300 become "intelligent" as a network with advanced sensors, controls, and software applications. Using such an infrastructure, advanced analytics can be provided to associated data. The analytics combines physics-based analytics, predictive algorithms, automation, and deep domain expertise. Via the cloud 320, devices 310-312 and associated people can be connected to support more intelligent design, operations, maintenance, and higher server quality and safety, for example.

Using the industrial internet infrastructure, for example, a proprietary machine data stream can be extracted from a device 310. Machine-based algorithms and data analysis are applied to the extracted data. Data visualization can be remote, centralized, etc. Data is then shared with authorized users, and any gathered and/or gleaned intelligence is fed back into the machines 310-312.

d. Data Mining Examples

Imaging informatics includes determining how to tag and index a large amount of data acquired in diagnostic imaging in a logical, structured, and machine-readable format. By structuring data logically, information can be discovered and utilized by algorithms that represent clinical pathways and decision support systems. Data mining can be used to help ensure patient safety, reduce disparity in treatment, provide clinical decision support, etc. Mining both structured and unstructured data from radiology reports, as well as actual image pixel data, can be used to tag and index both imaging reports and the associated images themselves.

e. Example Methods of Use

Clinical workflows are typically defined to include one or more steps or actions to be taken in response to one or more events and/or according to a schedule. Events may include receiving a healthcare message associated with one or more aspects of a clinical record, opening a record(s) for new patient(s), receiving a transferred patient, reviewing and reporting on an image, and/or any other instance and/or situation that requires or dictates responsive action or processing. The actions or steps of a clinical workflow may include placing an order for one or more clinical tests, scheduling a procedure, requesting certain information to supplement a received healthcare record, retrieving additional information associated with a patient, providing instructions to a patient and/or a healthcare practitioner associated with the treatment of the patient, radiology image reading, and/or any other action useful in processing healthcare information. The defined clinical workflows can include manual actions or steps to be taken by, for example, an administrator or practitioner, electronic actions or steps to be taken by a system or device, and/or a combination of manual and electronic action(s) or step(s). While one entity of a healthcare enterprise may define a clinical workflow for a certain event in a first manner, a second entity of the healthcare enterprise may define a clinical workflow of that event in a second, different manner. In other words, different healthcare entities may treat or respond to the same event or circumstance in different fashions. Differences in workflow approaches may arise from varying preferences, capabilities, requirements or obligations, standards, protocols, etc. among the different healthcare entities.

In certain examples, a medical exam conducted on a patient can involve review by a healthcare practitioner, such as a radiologist, to obtain, for example, diagnostic information from the exam. In a hospital setting, medical exams can be ordered for a plurality of patients, all of which require review by an examining practitioner. Each exam has associated attributes, such as a modality, a part of the human body under exam, and/or an exam priority level related to a patient criticality level. Hospital administrators, in managing distribution of exams for review by practitioners, can consider the exam attributes as well as staff availability, staff credentials, and/or institutional factors such as service level agreements and/or overhead costs.

Additional workflows can be facilitated such as bill processing, revenue cycle mgmt., population health management, patient identity, consent management, etc.

III. Example Systems and Integrated Architectures and Associated Methods

In certain examples, a Healthcare Data Exchange can be implemented to connect content source and subscriber targets using an intelligent bus-based discovery/routing mechanism to create and provision cloud-based interfaces supporting a large inter-connected ecosystem (e.g., multiple Labs, Payers, HIEs, etc.). Example cloud-based interfaces can be created and provisioned such that multiple source systems (e.g., hospitals, ambulatory clinics, specialty clinics, etc.) can send a healthcare-specific message payload to be intelligently routed to a defined target system. In certain examples, a method of interface construction and provisioning includes a combination of user experience (UX) driven self-service and model driven auto-provision workflow. A factory-based model and method for interface definition and configuration provides a consistent mechanism to publish interfaces into a registry for provisioning and "hot-deployment" system initialization and startup.

In certain examples, de-identification (and subsequent re-identification) of protected health information (PHI) for use in partitioning (sharding) data helps enable faster and more optimal querying for patient and population analytics within a "Big Data" warehouse.

Certain examples provide a software-based method to secure transport of a message payload using an intelligent discovery process for public key infrastructure (PKI) security and trust certificates between the system (e.g., referred to as "IntelliLink") and multiple partner systems within the inter-connected ecosystem.

An ingestor mechanism parses healthcare-specific payload structures and creation of clinical data transfer objects (DTOs). Certain examples provide "Big Data" processing that manages high-volume and high-velocity healthcare data streams built upon a platform that enables web-scale processing and sharding of data. A streaming complex event processing (CEP) engine processes incoming healthcare data to generate analytics/insight, actions and alerts on pre-defined patterns in the data. A machine learning mechanism learns patterns of messages exchanges based on meta-data to provide contextual awareness and optimization when new systems are added to the healthcare ecosystem and networks.

Utilizing the design and infrastructure described above, a Referrals system can be provided to enable Intelligent Care Connections that are optimized for a patient's convenience and outcome. Certain examples enable a fanning out of referral requests to multiple specialists concurrently to solicit bids that can be evaluated by patients.

Certain examples provide a mechanism that automatically discovers and builds a graph of the connected healthcare ecosystem that includes for relationships such as: People-to-people, Patient-to-Provider, Provider-to-Subcontractor, System-to-Interfaces, Message-to-System, Machine-to-Machine, Patient-to-provider visits, Specialist-to-location, Referrals-to-Outcome, etc. Certain examples can anticipate traffic congestions and bottlenecks in the healthcare ecosystem/environment and provide suggestions to care providers and patients. Certain examples can drive frictionless data exchange setup and provisioning of new interfaces by learning from previous setups.

Utilizing the design and infrastructure described above, a reference realization of a Cloud-deployed Lab Hub providing IHE standards-based connectivity between CIS, LIS and laboratory automation system (LAS) can be provided.

Certain examples provide a reference realization of a remote ICU monitoring solution (tele-ICU) which allows an intensivist at the command center to monitor real-time device parameters of critically ill patients from remote ICUs/Hospitals on a 24 hour /7 days a week basis.

Cloud-based integration (also known as integration platform as a service or IPaaS) is a form of systems integration delivered as a cloud service that addresses data, process, service-oriented architecture (SOA) and application integration use cases. Healthcare integration in "the cloud" is improved by optimizing connections within a healthcare ecosystem and by driving better patient outcomes, for example. Healthcare integration is facilitated via an intelligent switchboard and matchmaker focused on driving tighter connections in the healthcare ecosystem and improving the patient outcome and experience. Below is an example architecture which is explained in greater detail in subsequent sections along with example solutions which can be built on it.

Figure 4:
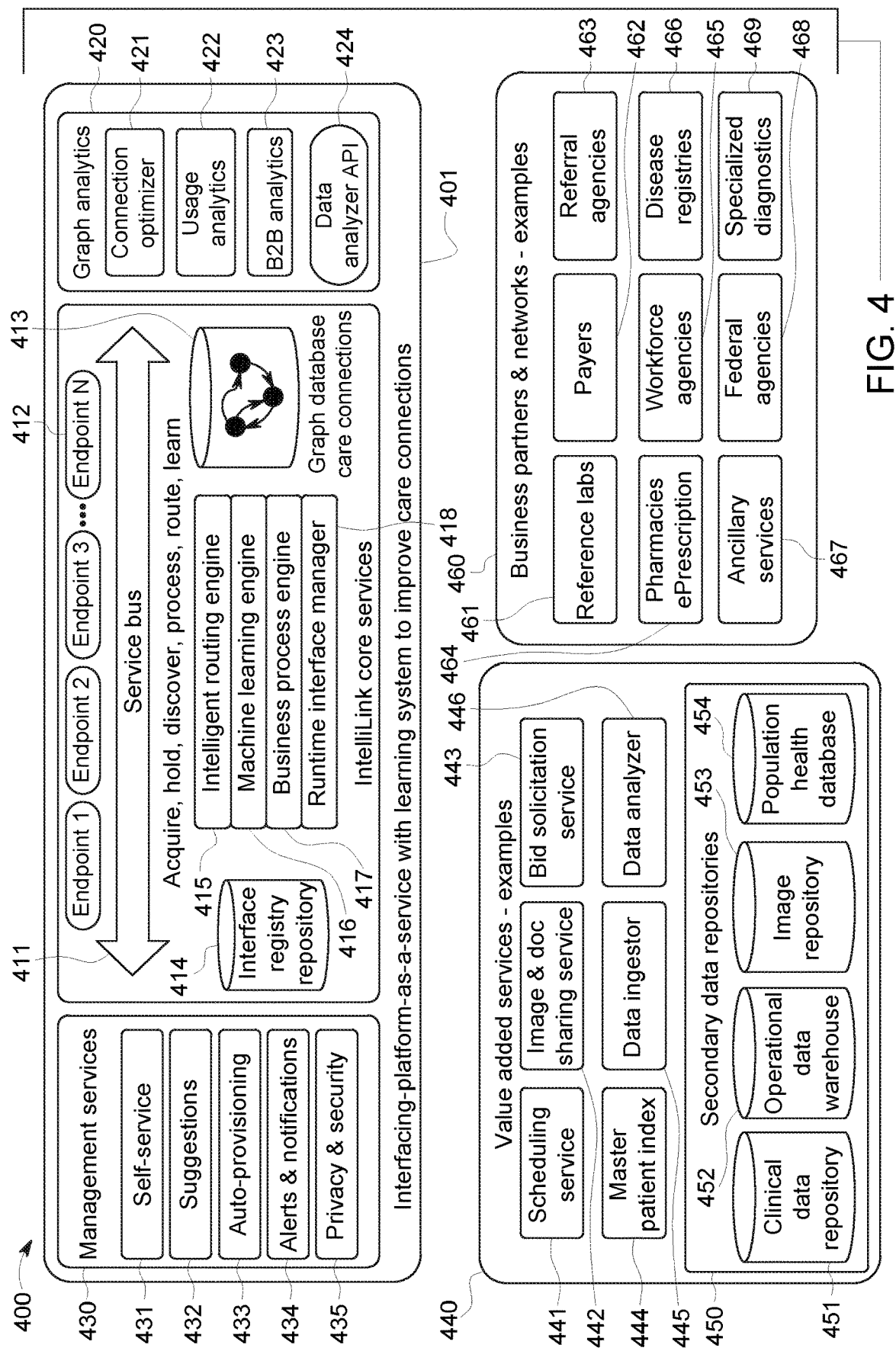
FIG. 4 illustrates an example architecture facilitating improved connection in a healthcare ecosystem.

FIG. 4 illustrates an example architecture 400 facilitating improved connection in a healthcare ecosystem. The example architecture or system 400 includes an interfacing platform-as-a-service (PaaS) 401 with learning system to improve care connections. The interfacing PaaS 401 includes IntelliLink core services 410, graph analytics 420, and management services 430.

The IntelliLink core services 410 are core components that facilitate systems integration in the cloud and that enable new systems to be integrated rapidly and easily. Endpoints 1 to N 412 can communicate with the IntelliLink core services 410 via a service bus 411. An Interface Registry and Repository 414 stores reusable interface and route definitions that are loaded by a Runtime Interface Manager 418 to enable message translation and exchanges. A Machine Learning Engine 416 monitors message exchanges and patterns to learn about and predict traffic and utilization patterns which is used by a Connection Optimizer 421. The Runtime Interface Manager 418 and the Machine Learning Engine 416 work with an Intelligent Routing Engine 415 and a Business Process Engine 417 to acquire, hold, discover, process, route, and learn with respect to one or more connected systems to improve care connections via the IntelliLink core services 410. Metadata about connections in the healthcare ecosystem is stored and tracked in a graph database 413 which is used by the core analytics services 410 shown in FIG. 4.

The Connection Optimizer 421 is a suggestion engine which provides context based recommendations when healthcare providers and patients seek to engage with various healthcare providers and workers in a connected healthcare ecosystem. The Connection Optimizer 421 is included as part of Graph Analytics 420 along with Usage analytics 422, B2B (Business-to-Business) 423 analytics, and a Data Analyzer API (Application Programming Interface) 424.

The Usage 422 and B2B 423 analytics are used to provide details such as value propositions to unconnected healthcare providers and insight about how to improve patient movements in the connected ecosystem. A set of management services and software agents 430 are used to automate the provision of new systems and the integration process in a self-serve manner. Management services 430 includes self-service 431, suggestions service 432, auto-provisioning service 433, alerts and notification service 434, privacy and security service 435, etc.

The Interfacing PaaS 401 can be paired with value added services 440 and/or business partners and networks 460. Some example value-added services 440, as illustrated in the example of FIG. 4, include a scheduling service 441, an image and document sharing service 442, a bid solicitation service 443, a master patient index 444, a data ingestor 445, and a data analyzer 446. Additionally, one or more secondary data repositories 450 can be include in the value-added services 440, such as a clinical data repository 451, an operational data warehouse 452, an image repository 453, and a population health database 454, for example.

As illustrated in the example of FIG. 4, some example business partners and networks 460 can include reference labs 461, payers 462, referral agencies 463, pharmacies/ePrescription 464, workforce agencies 465, disease registries 466, ancillary services 467, federal agencies 468, and specialized diagnostics 469.

Figure 5A:
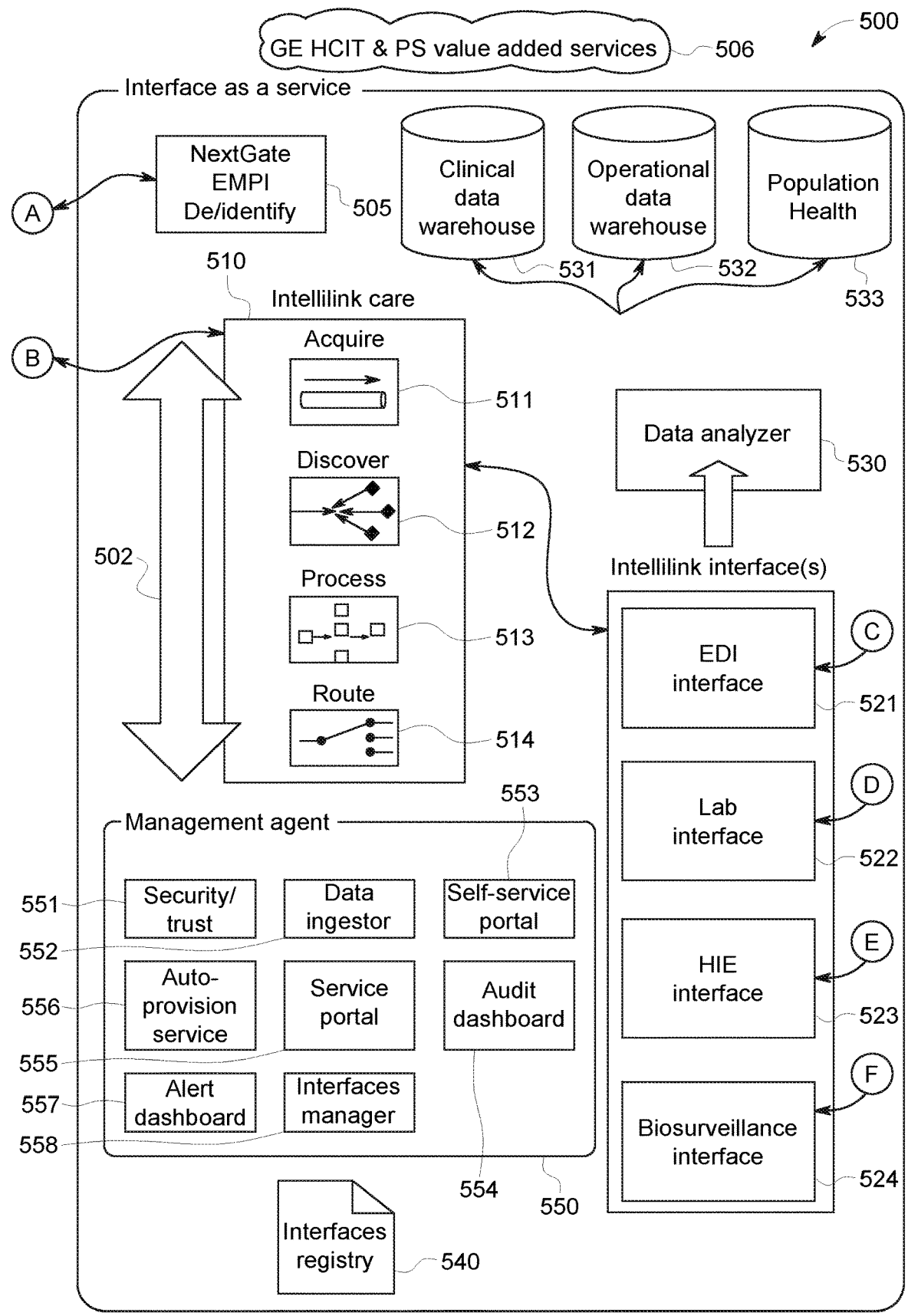
FIGS. 5A-5C illustrate IntelliLink Core Services provided as an Interface as a Service including a scalable integration bus and messaging fabric.
Figure 5B:
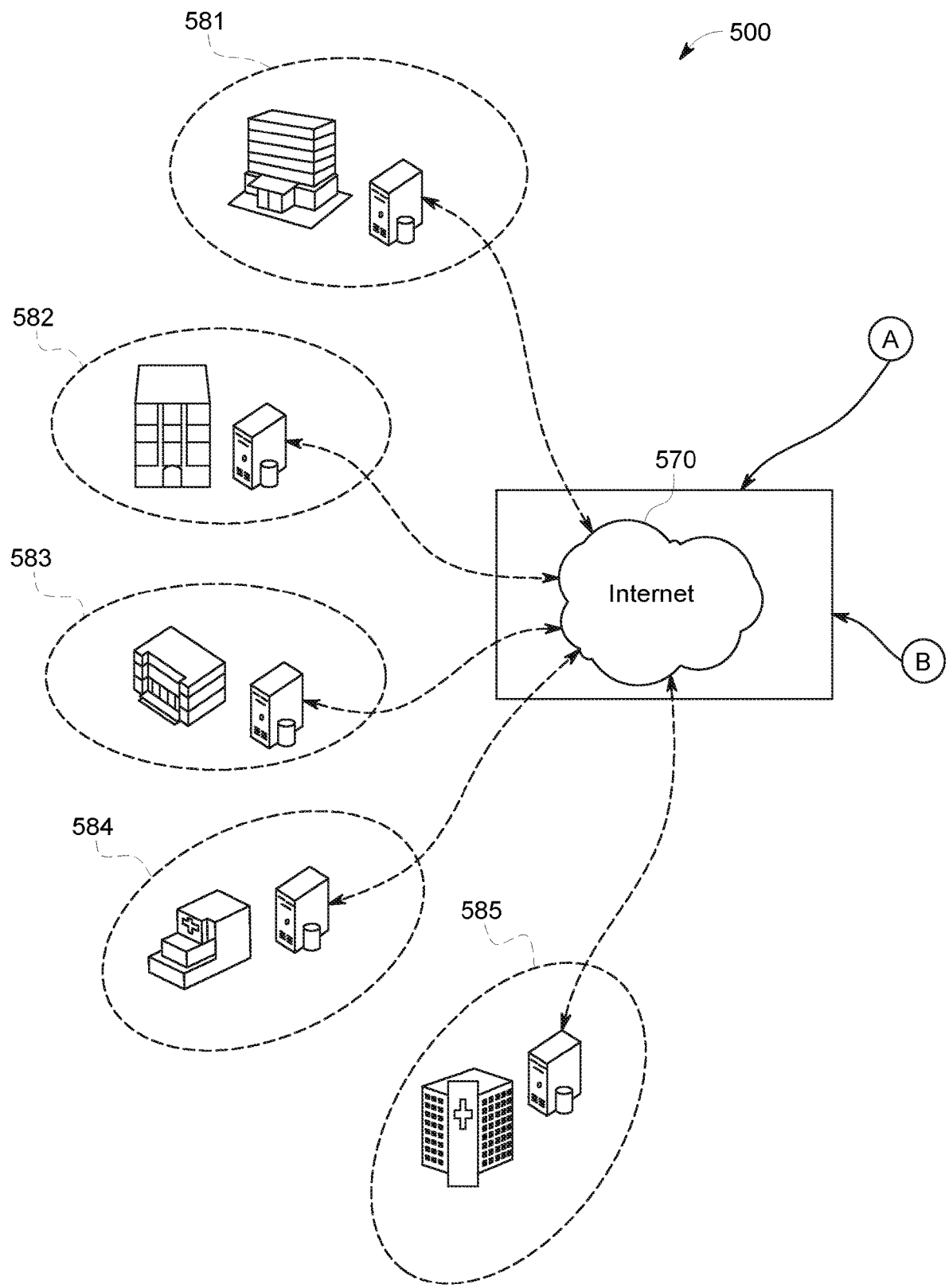
Figure 5C:
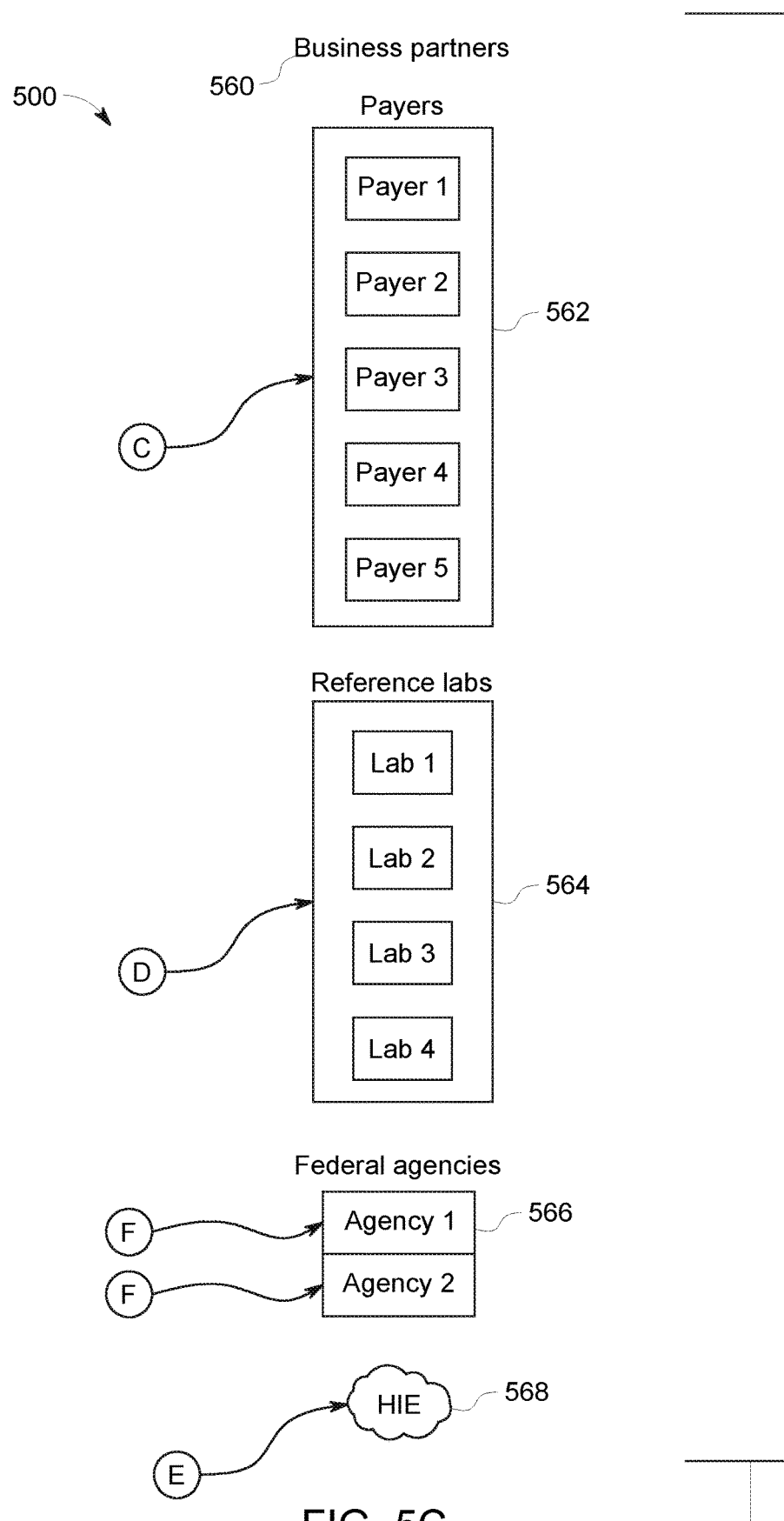

FIGS. 5A-5C illustrate IntelliLink Core Services 500 provided as an Interface as a Service (IaaS) 501 including a scalable integration bus and messaging fabric. As shown in FIGS. 5A-5c, for example, a scalable integration bus 502 (for example, Apache™ Camel, RabbitMQ, etc.) is deployed in a cloud fabric (e.g., with respect to a network 570) providing connectivity between source system(s) deployed within Hospitals, Ambulatory and/or Specialty Practices and Clinics 581-585 that should be able to exchange healthcare relevant clinical and/or non-clinical information with target system(s). A target system can include one or more of a set of business partner systems 560 (such as Payers 562, Labs 564, Clinics, Specialists, Healthcare Service Providers, federal agencies 566, etc.) that can send back a meaningful response which the source system embeds into its business processing logic and/or workflow. The IntelliLink bus 502 is deployed in the cloud 570 (for example, Microsoft™ Azure or Amazon™ EC2) that hosts the integration solution and provides the software runtimes and other infrastructure components and other non-relational storage services. Details on the bus 502 including the intelligent mediation that it facilitates are detailed with respect to FIG. 4 above.

As shown in the example of FIG. 5A, the IntelliLink Core Services Interface 501 includes a "core" Bus component 502 with a series of message processing pipelines 510 that is logically abstracted into the following tiers: message acquisition 511, message discovery (e.g., normalization/enrichment) 512, message processing (e.g., mediation) 513 and routing 514. Pluggable interface components 520 complement the core with each interface 521-524 being a logical unit that encapsulates the transformations and messaging workflow of the target system that is to be connected to the Bus 502 via plug-and-play connection. For example, as shown in FIG. 5C, an electronic data interchange (EDI) interface 521 allows one or more payers 562 to interface with a data analyzer 530. A lab interface 522 allows one or more reference labs 564 to interface with the data analyzer 530. A health information exchange (HIE) interface 523 allows an HIE 568 to interface with the data analyzer 530. A biosurveillance interface 524 allows one or more federal agencies 566 to interface with the data analyzer 530. The data analyzer 530 facilitates data analysis and storage with respect to one or more of a clinical data warehouse 531, an operational data warehouse 532, a population health data store 533, etc., based on interaction with one or more external partners 560 via their respective interfaces 521-524.

Pluggable interfaces 520 allow the IaaS 501 to logically and physically distinguish between the core component 510 that does specific actions such as authentication, secured data acquisition, interfaces discovery, message canonicalization, message content enrichment, message filtering, message mediation, content-based routing, error management and message replay, and the interfaces component 520, one for each target system that is to be connected, and that is specifically tailored to suit the message processing and protocol translation specific for that product or system. An interfaces registry 540 tracks the pluggable interfaces 520 and their target system connectivity.

A management agent 550 provides a plurality of management functions such as security/trust 551, data ingestor 552, self-service portal 553, audit dashboard 554, service portal 555, auto-provision service 556, alert dashboard 557, interfaces manager 558, etc., in conjunction with the core processing pipelines 510.

An enterprise master patient index (EMPI) 505 facilitates patient data de-identification and/or re-identification with respect to one or more external sites 581-585 via a network 570. Thus, as shown in FIG. 5B, one or more hospitals 581, 582, 585, special practice 583, clinic 584, etc., can communicate with the IaaS 501 via the network 570 (e.g., the Internet, intranet, virtual private network, and/or other network). Additionally, one or more value added services 506 can be provided in conjunction with the IaaS 501.

Figure 6A:
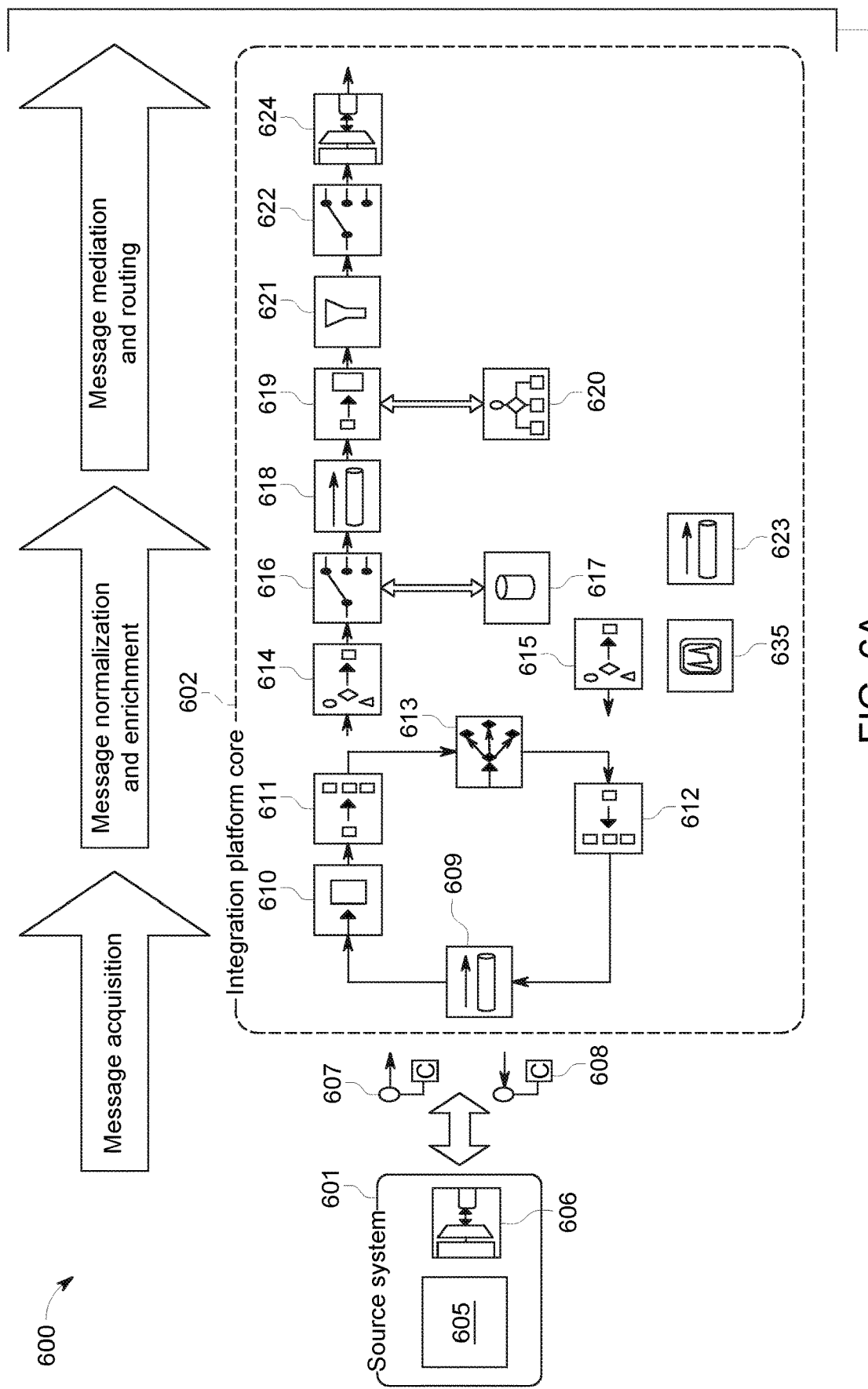
FIGS. 6A-6B illustrate an example enterprise integration patterns schematic for intelligent routing via an IntelliLink bus.
Figure 6B:
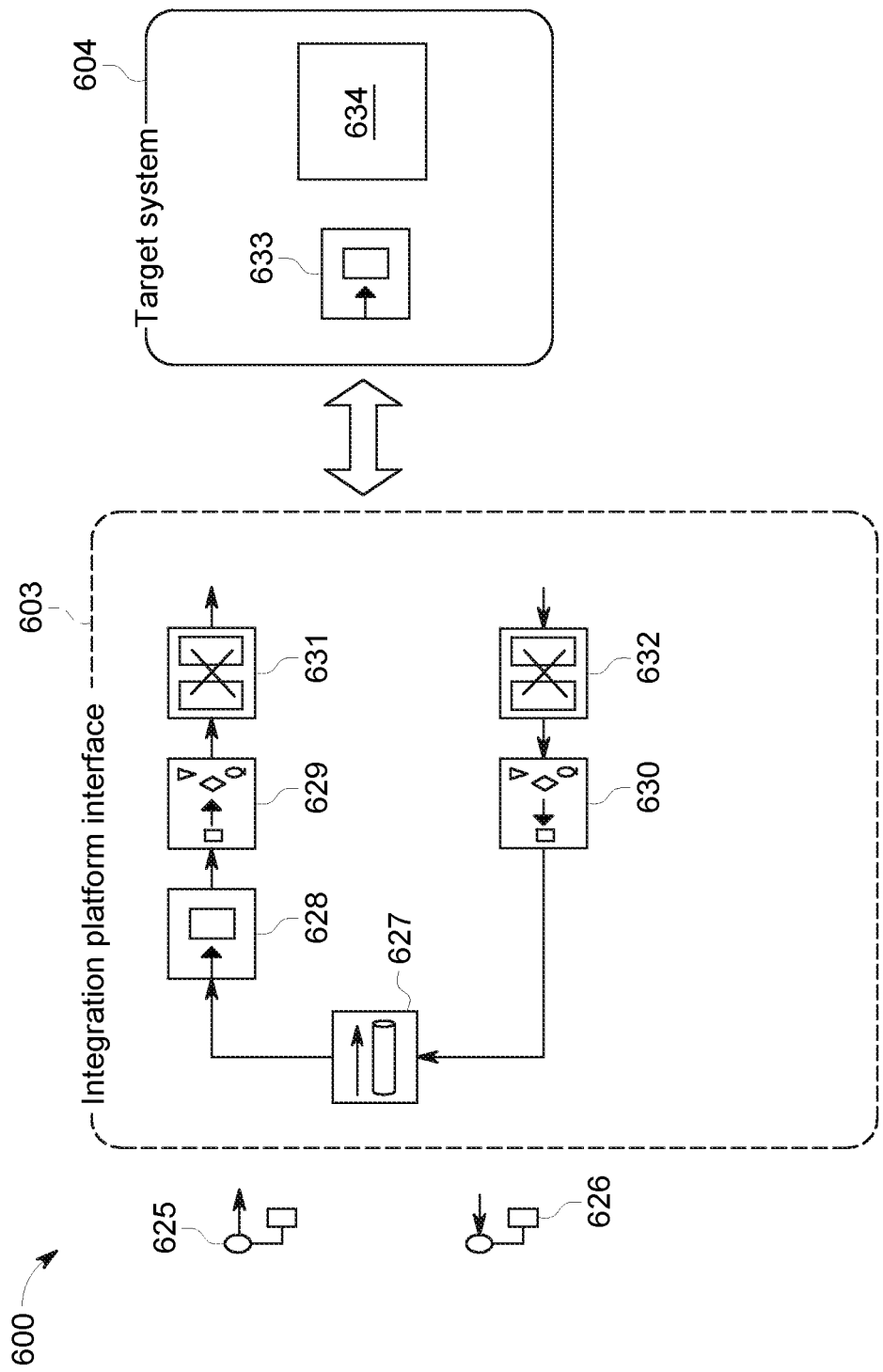

FIGS. 6A-6B illustrate an example enterprise integration patterns (EIP) schematic 600 for intelligent routing via the IntelliLink bus 502. The EIP schematic 600 shows a plurality of logical and physical tiers within the system demarcated by a core intelligent routing engine 602 and several plug-on interfaces 603. To enable message exchange to the "Bus" 602, a channel adapter 606 at a source system's 601 service layer (SL) 605 is used as a messaging client to construct and publish messages for consumption by an interface endpoint service 603 fronted by an IntelliLink message acquisition service.

The interface endpoint service 603 adheres to contractually defined request/response types (e.g., represented by eXtensible markup language (XML) schema definition (XSD) complex schema types) and should speak a variety of protocols such as Health Level Seven (HL7), Simple Object Access Protocol (SOAP), XML/HTTP, Representational State Transfer (REST) or Common Object Request Broker Architecture (CORBA) and work over a variety of transports such as Transmission Control Protocol (TCP) (e.g., TCP (MINA)), Hypertext Transfer Protocol (HTTP), Java Message Service (JMS), Advanced Message Queuing Protocol (AMQP), Data Distribution Service (DDS), Constrained Application Protocol (CoAP), and Java Business Integration (JBI).

An IntelliLink message acquisition channel or gateway 609 uses a message channel enterprise integration pattern in which a source application 601 sends command messages 607 to a message channel 609 that acts as a facade. The message is normalized 614 into a canonical data model with associated meta-data, enriched 619 with content from external data sources and mediated across the logical tiers to be intelligently routed 622 to an interface message channel 624. The message acquisition channel is exposed as a coarse-grained service that performs secured message acquisition from client sources and passes it onward to further distributed processing downstream eventually routing the message (canonicalized into a standard format) to the interface channel 624. The interface message channel service 627 is more fine-grained and intelligently structured to suit the logical and message protocol needs of the target system 604 that is the final destination of the normalized, canonical data formatted request message 625. Interface implementations support healthcare standard protocols such as HL7 v2.x/3.x, Clinical Document Architecture (CDA) and Integrating the Healthcare Enterprise's (IHE's) Cross-Enterprise Document Sharing (XDS), Patient Identity Cross-Referencing/Patient Demographics Query (PIX/PDQ), Audit Trail and Node Authentication (ATNA), HL7 Fast Healthcare Interoperability Resources (FHIR), and other IHE profiles. The IntelliLink platform enables a common, shared governance model representative of an inter-connected product landscape to provide for consistent system initialization and interface provisioning.

IntelliLink includes a powerful routing/mediation engine. IntelliLink's routing engine defines routes and message processing pipelines encapsulating message flows and intermediary processing between endpoints. Routes are developed and configured with combinations of Enterprise Integration Patterns (EIPs) to implement mediation and routing rules with the help of Domain Specific Language (DSL) expressions and wired together. Processors are used to transform and manipulate messages during routing and to implement EIP patterns. The IntelliLink's message acquisition channel is provisioned, for example, either via a secured Web Service (WS)-* endpoint or a RESTful endpoint with a configured endpoint interface (and message contract) declaratively configured. In an embodiment, the message acquisition channel can also be available via a TCP (MINA) endpoint that can be configured to receive HL7 v2.x messages.

As shown in the example of FIG. 6A, the message acquisition channel 609 receives a command message 607 encapsulating the message payload along with metadata about the specific interface endpoint to which the message is to be routed. IntelliLink core 602 has been designed with intelligent message processing pipelines and intermediary processing (e.g., platform message endpoint 610, splitter 611, dispatcher 613, normalizer 614, dynamic router 616, configured rules base 617, message processor channel 618, content enricher 619, process manager 620, filter 621, content-based router 622, interface channel adapter 624) that facilitate unmarshalling of the wrapped message payload and intelligent content-based routing of the message to the interface subscriber. An interfaces control channel 623 can control the platform message channel 609, message processor channel 618, interface channel adapter 624, etc., based on available channel(s) and/or other parameters, constraints, etc.

As shown in FIG. 6B, the integration platform interfaces 603 provide an interface message channel 627 receiving the normalized canonical message 625 and, through an interface message endpoint 628, de-normalizing 629 and translating 631 the message 627 for the target system 604 which receives the message at an endpoint 633 and interacts via a service layer 634.

An outgoing message from the target system 604 is received by a translator 632, re-normalized 630, and provided back to the core 602 via the interface message channel 627 as a normalized canonical data format response 626. The core 602 also includes a de-normalizer 615 and an aggregator 612 to dispatch 613 messages via the platform message channel 609 as a response message 608 from the target system 604 back to a source channel adapter 606 and service layer 605 of the source system 601. As shown in the example of FIGS. 6A-6B, a platform manager 635 can be provided to coordinate and/or otherwise control message acquisition, message normalization and enrichment, and message mediation and routing via the example system 600.

As illustrated in the interface design example of FIGS. 6A-6B, every interface is deployed with at least three components: a message endpoint, an interface configuration, and an interface factory. As illustrated further with respect to the example of FIG. 7, the message endpoint q is defined within an interface route 717 that is tailored specifically for the workflow of that interface and encapsulates message processing and protocol translation to invoke the target system. The interface configuration qn 712 includes pre-defined message contracts that define what the interface expects to receive in terms of message content as well as the message the interface expects to receive in terms of message content and the message the interface expects to send back in response after invocation of the target system 604. An interface factory 711 returns concrete instances of the interface route 717 and interface configuration 712.

Figure 7:
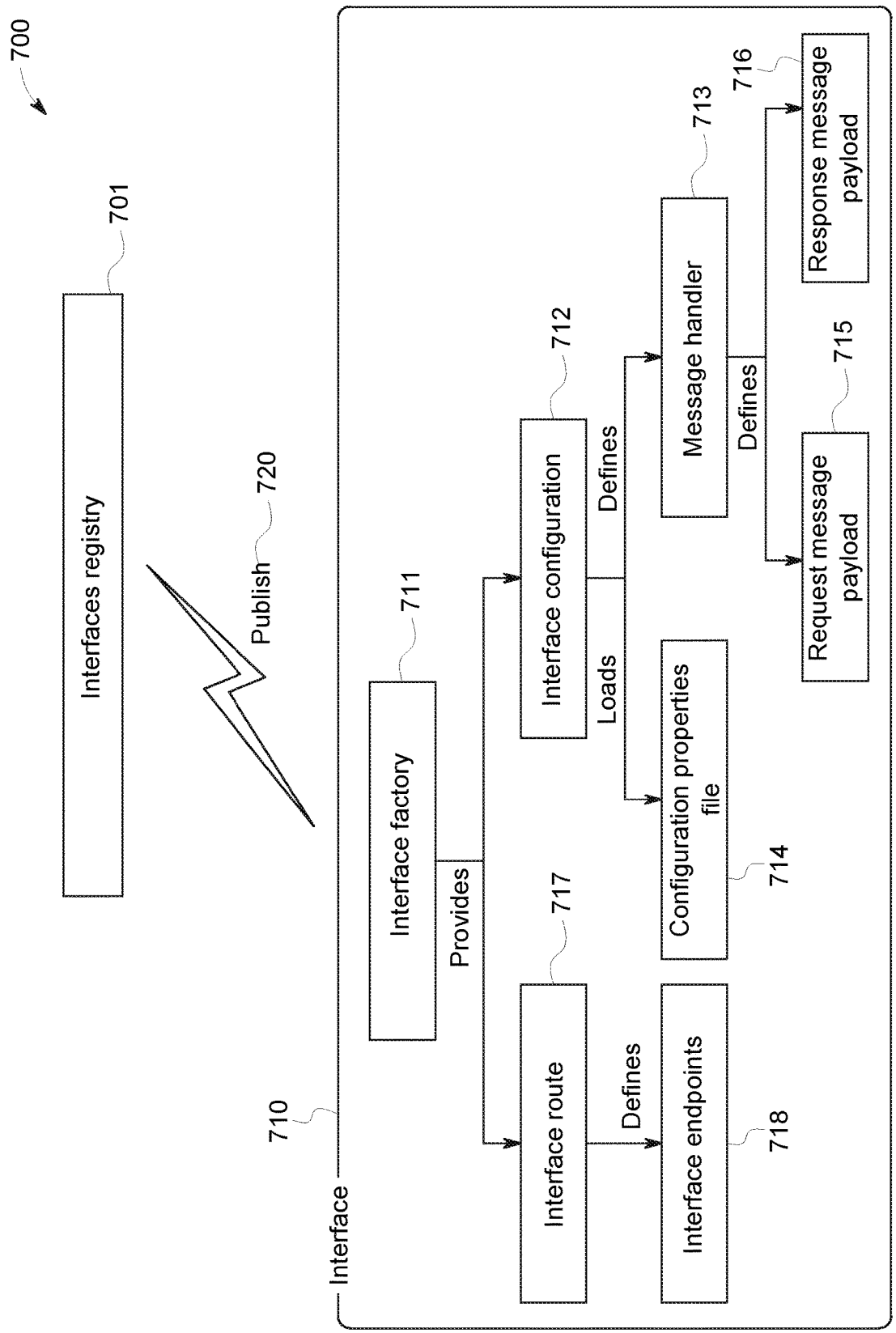
FIG. 7 illustrates a system providing an example factory-based model for interface definition and configuration.

FIG. 7 illustrates a system 700 providing an example factory-based model for interface definition and configuration. The example system 700 publishes 720 one or more interfaces 710 into an interface registry 701 for consistent provisioning and "hot-deployment" system initialization and startup. In an example, an interface configuration 712 is loaded from an interface properties file 714 (e.g., structured in XML) that includes, among other elements, a message handler 713 implemented as a parameterized class that defines request/response message object types 715, 716.

The interface 710 is designed to be pluggable onto the core platform component and as such can be implemented as a self-contained unit. Therefore, the configuration 714 associated with each interface 710 includes, in addition to the defined message in/out contracts, information to support a message processing and protocol translation specific for the target system to which the interface 710 serves as a facade. The information can include the target system's interface endpoint 718 uniform resource locator (URL) or other address information, a listing of callback services to enrich the original message passed in, for each callback. For example, query or search criteria and callback service URL(s), message filtering criteria and other business rule definitions specific for the target system that are to be applied to the message can be included.

The IntelliLink IaaS platform can then derive intelligence from configuration information contained within each "plugged-in" interface which includes a contractual input/output format types, rules for message enrichment (e.g., a listing of callback services to a calling system's service layer (and/or other third party systems via a Business Process Management (BPM) or Business Process Execution Language (BPEL) based process manager, etc.) along with query/search criteria for the callback action to be executed, additional business-level rules that govern message routing, and message filtering criteria to be applied, for example. The configuration can be implemented using XML syntax and/or in some examples, using custom expressions based syntax, and may be unique to each interface.

Figure 8A:
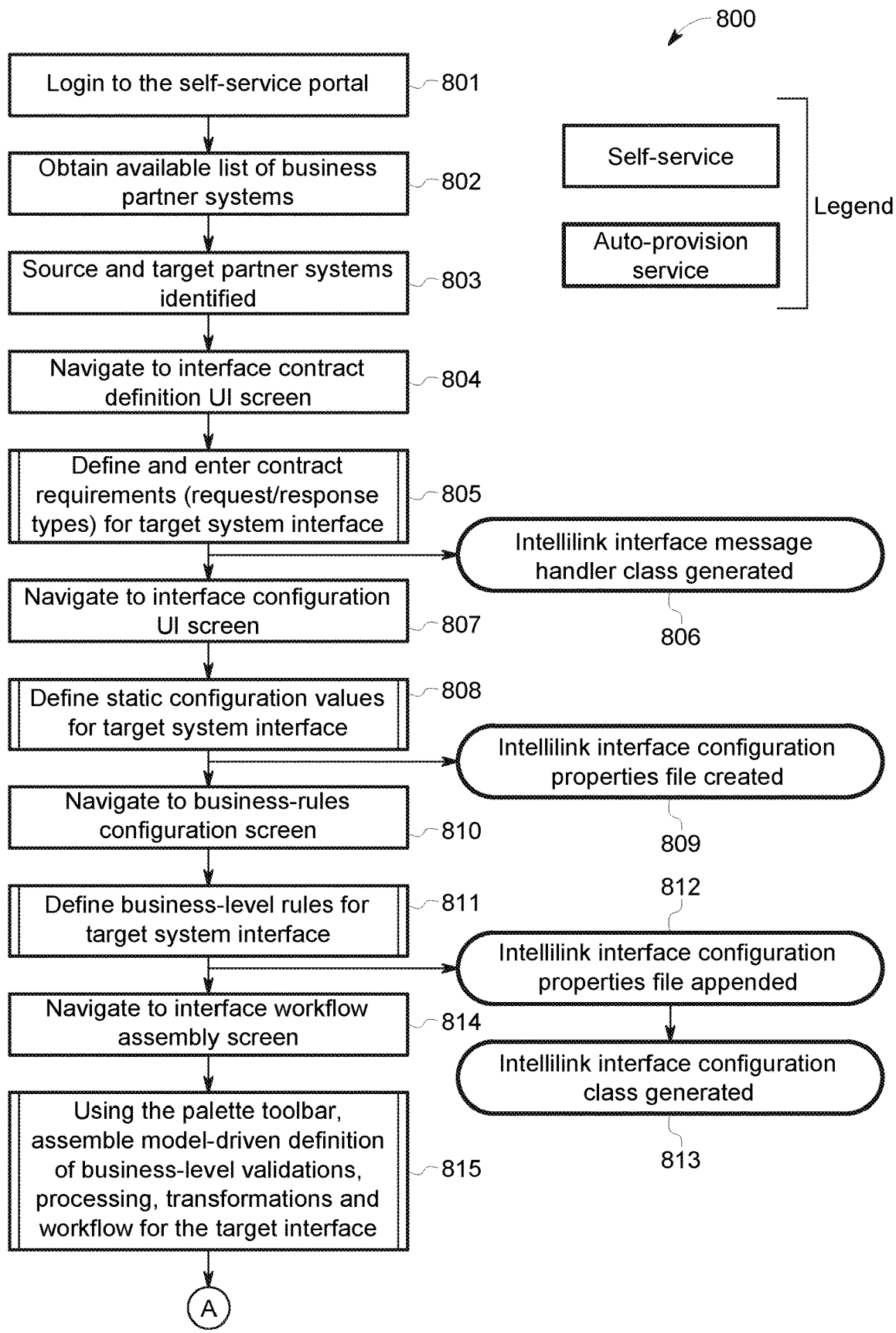
FIGS. 8A-8B illustrate a flow diagram of an example process or workflow to provision a new interface.
Figure 8B:
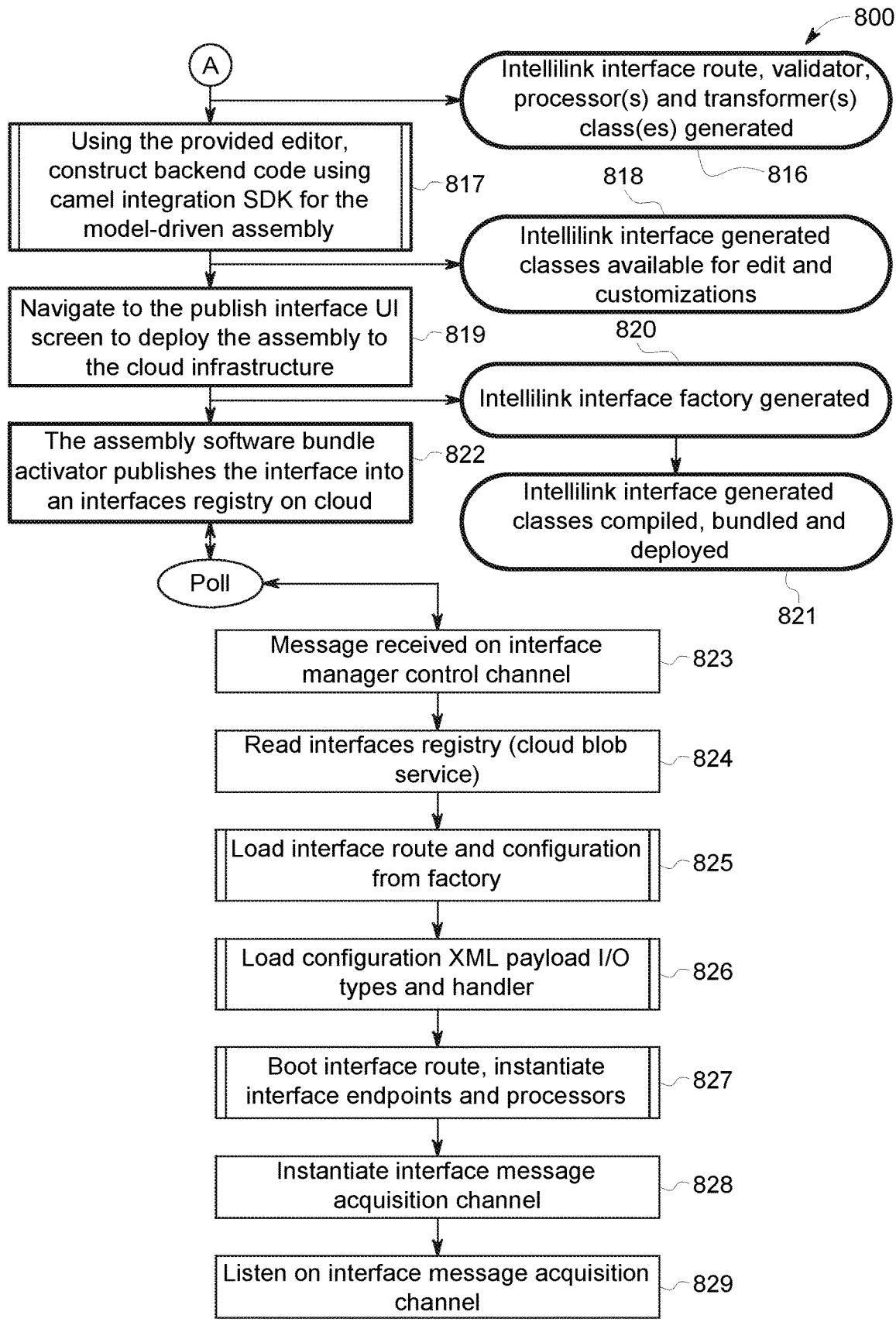

FIGS. 8A-8B illustrate a flow diagram of an example process or workflow 800 to provision a new interface. Creation of a new interface and provisioning the interface on the above-described cloud-based infrastructure includes a combination of a user initiated self-service request and model driven auto-provision workflow 800. At block 801, the workflow 800 is initiated from a self-service portal which is part of the solution. Initiation of the workflow 800 triggers a model-driven auto-provision service that generates artifacts and code to create and deploy the interface based upon the factory model of FIG. 7.

At block 802, a list of available business partner systems is obtained. For example, a list of one or more payers, labs, clinics, specialists, healthcare service providers, federal agencies, etc., is obtained. At block 803, based on the list of available business partner systems, source and target partner systems are identified. For example, a source partner system may be a payer (e.g., an insurance carrier, health plan sponsor, other third-party payer, etc.) and a target partner system may be a healthcare service provider (e.g., a specialist such as an Addiction psychiatrist, Allergist (immunologist), Cardiologist, Surgeons, Dermatologist, Gynecologist, Nephrologist, Neurologist, Occupational specialist, Oncologist, Pain management specialist, Physiatrist, Plastic surgeon, Psychiatrist, Radiologist. Rheumatologist. Sleep disorders specialist, Sports medicine specialist, Urologist, etc.).

At block 804, an interface contract definition interface screen is displayed. For example, a graphical user interface (GUI) on a laptop, desktop, handheld (e.g., smartphone, tablet, etc.) and/or other computing device can be used to display an interface to define an interface contract. At block 805, interface contract requirements are defined and entered (e.g., request/response types, etc.) for a target system interface. For example, type(s) and format to interface between systems (e.g., exchange a request for information and a corresponding response, etc.) can be defined and provided as part of an interface contract definition. At block 806, an interface message handler class is generated in response to the contract requirement definition. For example, an interface message handler class is generated according to the contract requirements to intercept requests and responses and process and route the request and response messages appropriately.

At block 807, an interface configuration GUI screen is displayed. For example, an interface is provided to allow a user to view and/or adjust configuration parameters for the interface (e.g., search criteria, protocol, format, sequence, brightness, contrast, window level, window arrangement, etc.). At block 808, via the interface configuration GUI, static configuration values for the target system interface are defined (e.g., type(s) of traffic handled, mode(s), address, access, etc.). At block 809, an interface configuration properties file is created based on the input definition for the interface configuration. The input definition can include the static configuration values, other configuration parameters and other interface definition information, for example.

At block 810, a business rules configuration screen is displayed. The business rules configuration screen allows a user to view and/or adjust business-level rules for the target system interface. At block 811, business-level rules for the target system interface are defined. For example, mapping rules, coding systems (e.g., medical terminology, etc.), privacy-related rules (e.g., checking whether a Business Associate Agreement exists, etc.) and the like can be defined to specify business-level operations and constraints for the target system interface. At block 812, the business-level rules are appended to the interface configuration properties file. Thus, the interface configuration properties file can include both an input interface definition/configuration and business-level rules to be applied to the target system interface. At block 813, an interface configuration class is generated based on the interface configuration properties file.

At block 814, an interface workflow assembly screen is displayed. The interface workflow assembly screen allows a user to view and/or adjust a workflow and associated definitions for the target system interface. For example, the interface configuration properties file including interface definition(s), configuration information, business-level rule(s), etc., can be processed to form a default workflow for the target system interface. Via the interface workflow assembly screen, the default workflow and/or associated definitions can be viewed, simulated (e.g., previewed, played out, etc.), and/or adjusted before being saved as a part of the interface configuration. At block 815, using a palette toolbar, a model-driven definition of business-level validations, processing, transformations, and workflow are assembled for the target interface. For example, the interface configuration properties file can be loaded and assembled, and the toolbar allows final tweaks and/or other modifications to the configuration and format. At block 816, interface route, validator, processor(s), and transformer(s) class(es) are generated. For example, class(es) are generated based on the definitions, properties, preferences, modifications, and/or other configuration information specified above.

At block 817, using an editor, backend code is constructed using, for example, a Camel Integration software development kit (SDK) for a model-driven assembly. For example, based on the classes, code is constructed to form the interface. At block 818, interface generated classes are available for edit and customization. For example, additional review, revision, and/or other customization can be provided at this stage.

At block 819, a publish interface GUI is displayed to facilitate deployment of the assembly to a cloud infrastructure. For example, the publish interface GUI can provide one or more options to review, modify, and/or publish an assembled interface for use by one or more target systems. At block 820, the interface factory is generated. The interface factory can generate interfaces according to the assembled interface model, for example. At block 821, interface-generated classes are compiled, bundled and deployed.

At block 822, the interface is published into an interface registry. For example, the interface may be published by an assembly software bundle activator. In certain examples, the interface may be published. The interface is then available for use.

At block 823, a message (e.g., a polling message for interface) is received on an interface manager control channel. At block 824, an interfaces registry (e.g., a cloud blob service) is read. At block 825, an interface route and configuration are loaded from the interface factory. At block 826, a configuration payload (e.g., an XML configuration payload) is loaded including input/output (I/O) types and handler. At block 827, an interface route is booted, and interface endpoints and processors are instantiated. At block 828, an interface message acquisition channel is instantiated. At block 829, the interface message acquisition channel is used to listen for incoming and/or outgoing messages. For example, one or more Health Level Seven (HL&) messages such as Patient Administration Messages (HL7 ADT), Orders (HL7 ORM), Charges (HL7 DFT), Results (HL7 ORU), Schedule information (HL7 SIU), Referral (HL7 REF), Image order, Pharmacy order, Clinical Documents (CDA), etc., can be received via the interface message acquisition channel. Additionally, HL7 Fast Healthcare Interoperability Resource (FHIR) messages such as encounter, order, medication, diagnostic, alert, etc., can be received via the interface message acquisition channel, for example.

In addition to the message acquisition channel, the IntelliLink core also provides an additional interface control channel. An Interface Manager component communicates on this additional interface control channel. At interface provisioning time, in an effort to announce its presence, each interface sends a message which is published to an interfaces registry. In an embodiment, the bundle activator for the newly deployed interface sends a message which wraps the interface factory resource path as it is published to the registry.

In operation, the registry can be stored within a cloud storage service (for example, the Azure Blob storage service or Amazon S3) to be shared across the service fabric in deployment. During system start-up and during a periodic polling window to support "hot deployment", this registry is read by the interface manager, and the concrete instances of the interface route and configuration classes are loaded from the factory. The interface configuration is loaded, and the interface route is booted up and the endpoints instantiated. Business level rules applicable to the interface implementation that govern the routing of the message are then be populated into a rule base in a cloud relational database (RDB) (for example, SQL Azure or Amazon RDB, etc.). At system start time, in addition to reading configuration settings that control behavior of the interfaces and booting the interface routes, the interface manager also boots all the intermediate core camel routes involved in message processing and routing, for example.

Figure 9:
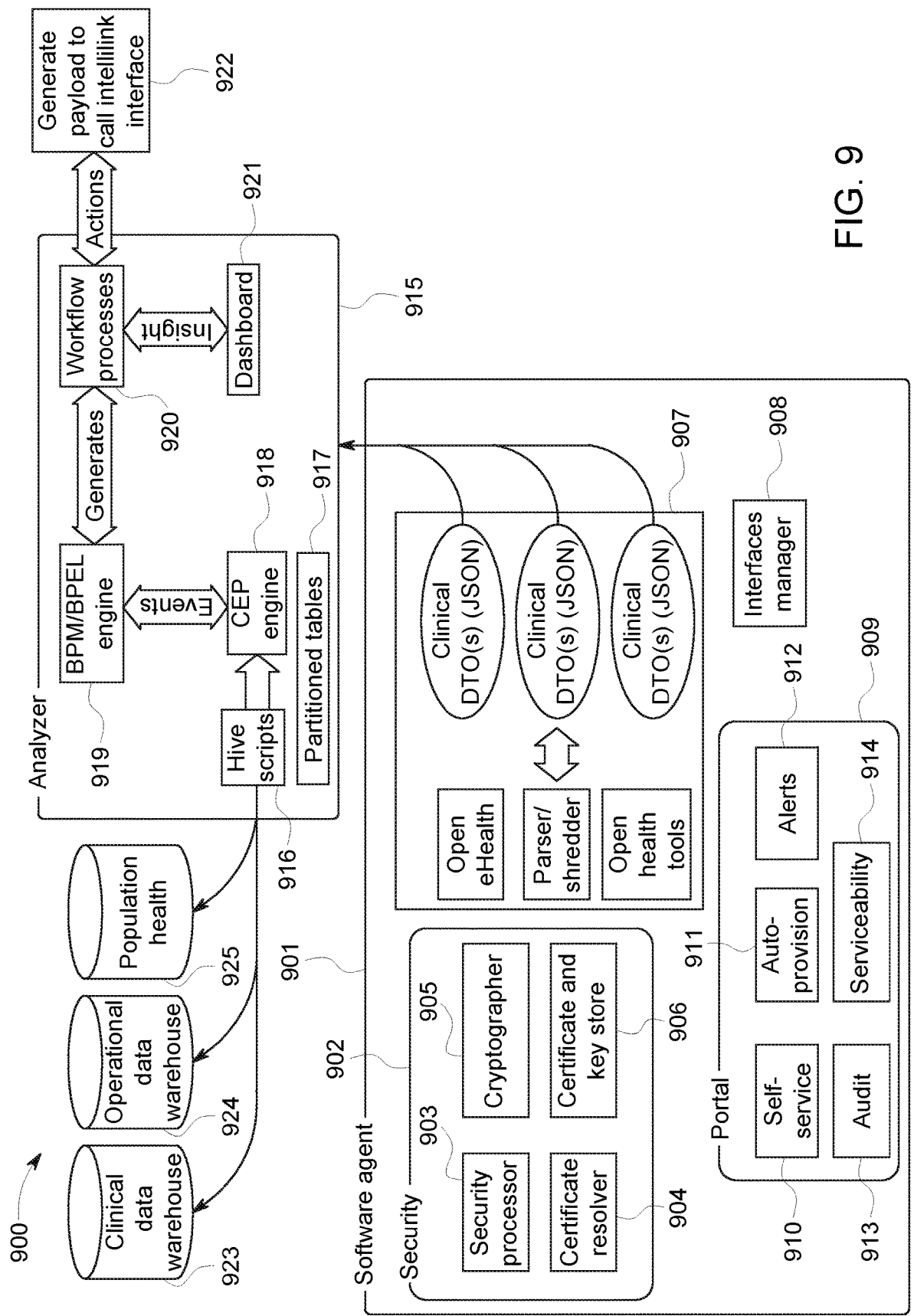
FIG. 9 depicts example software agent and management services use to fulfill certain core interface functions and adjacencies.

FIG. 9 depicts example software agent and management services 900 used to fulfill certain core interface functions and adjacencies. For example, a software agent module 901 (deployed on the cloud along with IntelliLink) can be used in conjunction with IntelliLink to fulfill certain core functions and adjacencies such as security, data ingestion, automatic interface provisioning, service portal, alerts and audit. The software agent 901 includes an interfaces manager 908 to facilitate interaction with one or more provisioned interfaces.

As shown in the example of FIG. 9, a software agent 901, data ingestor 907, and analyzer 915 are provided. Several components are involved, and each component within the software agent 901 functions independently while the agent 901 orchestrates the interplay between components. For example, a security module 902 inspects and processes security credentials of all outgoing/incoming messages to the various external partner systems that are deployed within the IntelliLink ecosystem.

In an example, the security component 902 is deployed as a software bundle that is plugged in when IntelliLink and the core messaging routes are initialized. The security unit 902 intercepts and processes outgoing messages to be signed and encrypted according to the security and trust specification defined between IntelliLink and the partner system. Inversion of Control (IoC) and Dependency Injection (DI) patterns can be used for various components to switch bindings, providers and modules, for example. Some core components within the Security module 902 that would be loaded via IoC and DI include: a security interceptor 903, a cryptographer 905, and a certificate resolver 904, as well as a certificate and key store 906.

The security interceptor 903 is an agent implementation of the message processor that processes incoming and outgoing messages according to a defined security and trust specification. The cryptographer 905 is a cipher suite implementation for message encryption/decryption and message signature operations. The certificate resolver 904 is responsible for discovering (and locating) public and private X509 certificates and keystores for target destination systems working in concert with a trust enforcement policy via trust anchors and revocation policies. The security module 902 enforces the security model helping to ensure that all IntelliLink interface endpoint recipients have valid certificates and that IntelliLink is allowed to send to each recipient according to the trust policy. The message is signed using a certificate and private key generated for IntelliLink. The message is encrypted using a random symmetric key and the symmetric key is encrypted using the recipient target system's public key, the certificate for which has been prior loaded into the system keystore and located by the certificate resolver 904. Similarly, on the response side, the agent module 901 decrypts the message 905 using a private certificate of the recipient and an encrypted symmetric key. Additionally, the message signature from the target system is also validated using the senders' public certificate 904, 906.

As shown in the example of FIG. 9, a data ingestor component 907 is used to shred and parse clinical data content received. If the content payload is a valid consolidated clinical document architecture (CCDA) document or lab order, for example, then the component 907 uses, for example, Open Health Tools APIs to parse the structure to extract certain common clinical DTO elements. For example, the CCDA can be parsed on an allergies section context to extract allergen substance(s), adverse reactions, reaction observation, status observation and severity observation. Similarly, problem sectional context can also be parsed to extract problem(s) observation, age observation, health status and problem status. Likewise, medication sectional context can be parsed to extract medication(s), drug vehicle, indication, instructions, medication dispense, medication information, medication supply order, preconditions, reaction observation. Along with certain sections that are mandated by CCDA such as allergies, problem list, medications, procedures and results, etc., certain optional sections can also be parsed such as: advance directives, encounters, family history, functional status, immunizations, medical equipment, payers, plan of care and vital signs. The clinical DTOs are produced in JavaScript Object Notation (JSON) format and aggregated. The aggregated objects are then pushed into a data analyzer platform 915.

The data analyzer platform 915 manages high-volume and high-velocity data streams quickly and efficiently in a fault-tolerant manner by leveraging Big Data technologies. Distributed Big Data architectures such as Hadoop differ from contemporary data warehouse/business intelligence architectures. Hadoop is an open-source framework for running applications on large clusters of commodity hardware with distributed nodes and offers an efficient, automatic distribution of data into Hadoop Distributed File System (HDFS), a highly fault-tolerant distributed file system akin to GFS, Google's proprietary file system. Hadoop features high fault tolerance and reliability wherein large files are split into smaller equal sized blocks, spread across the cluster and replicated to avoid the failure of single machines and speed up processing.

In addition, the data analyzer 915 also includes an implementation of a functional programming model, such as MapReduce, which is suitable for parallel processing of large amounts of data by partitioning 917 data into a number of independent chunks. Complementing Hadoop/HDFS, a broad class of DBMS and warehousing tools can be used to store varied broadly classified data types such as: structured, semi-structured and unstructured data. For example, Apache HBase is an open-source non-relational database modeled after Google's Big Table and runs on top of HDFS providing Big Table-like storage capabilities with automated and configurable sharding of tabular data. Apache Hive offers Big Data warehousing tools 916 to enable ETL on data stored either in HDFS or in other storage systems such as Hbase. It uses a simple SQL-like query language called HiveQL with the actual query execution spawning a MapReduce job.

In certain examples, the data analyzer 915 is built upon Amazon Elastic MapReduce. Amazon Elastic MapReduce is a Web service that enables easy and web-scalable processing of vast amounts of data. Amazon Elastic MapReduce utilizes a hosted Hadoop framework running on the web-scale infrastructure of Amazon Elastic Compute Cloud (EC2), Amazon Simple Storage Service (S3) and Apache Hive. Amazon Elastic MapReduce allows focus on crunching or analyzing data without time (and cost) consuming set-up, provision, management or tuning of Hadoop (Hive) cluster or the compute capacity on which they sit. The data ingestor component 907 is involved in parsing out clinical content and extracting DTOs in JSON format. The extracted clinical JSON records are stored one per line in a log file. Storing the records in the log file makes it easy to import into Hive as the records can be read using a default text format (e.g., Serde). The JSON files are then pushed by the ingestor 907 for temporary storage (e.g., into Amazon S3).

An Amazon Elastic MapReduce job flow then imports the log files into a partitioned table 917 within Hive 916. Using a partitioning table 917 allows queries to be specified that only read a subset of the data rather than causing Hive 916 to do a full table scan. One partitioning strategy uses a current date and a sub-partition on Master Patient Index (MPI) which segregates the clinical elements present by date and patient identifier for easier and faster querying. Various Hive scripts 916 can then be used on the resultant "raw data" to generate intermediate data and populate tables with the "reduction result". The data can be analyzed directly, loaded into other unstructured databases and/or merged into a clinical data warehouse and/or an operational data warehouse 923, 924, 925 and correlated with structured data. In a traditional data warehouse 924, 925 environment, conventional business intelligence reporting, statistical, semantic and correlation capabilities can be leveraged.

In certain examples, scripts 916 processing data in the partitioned tables 917 in conjunction with a complex event processing (CEP) engine 918 and a BPM/BPEL engine 919 to generate one or more workflow processes 920. The workflow process(es) 920 can provide insight to a user and/or other system via a dashboard 921 (e.g., providing a visual display, reporting, interaction, etc.). The workflow process(es) can also facilitate action to generate a payload 922 to call an IntelliLink interface, for example.

Certain examples provide a service portal 909 to manage a deployed messaging infrastructure and configured routes. The example service portal 909 includes a self-service component 910, an auto-provision service component 911, an alert component 912, an audit component 913, and a serviceability component 914. The service portal 909 provides a consolidated dashboard view of all the interfaces that have been deployed in the ecosystem. The consolidated dashboard view also displays meta-information and related metrics regarding each interface state, message(s) transmitted, message(s) failed/errored, last complete time, etc. User interface buttons and associated click-events on the interface route dashboard start and stop the interface routes, thereby providing fine-grained control and administration on the deployed interfaces. A message monitor dashboard view shows inbound and outbound messages that have been routed through to the interface. The message monitor dashboard provides filter-based views against the database to obtain the messages that fulfill certain pre-defined criteria such as start/end dates, errored messages, all messages, etc.

In certain examples, a graph database of care connections (e.g., OrientDB, Neo4J, AllegroGraph, etc.) is used to store relationships within the healthcare ecosystem. Such relationships may include but are not limited to: people-to-people, patient-to-provider, provider-to-subcontractor, system-to-interfaces, message-to-system, machine-to-machine, patient-to-provider visits, specialist-to-location, diagnosis-to-treatment, referrals-to-outcome, patient-to-location, provider-to-specialist, organization-to-organization, business-to-business and authorized-connections, etc.

Graph databases apply graph theory to the storage of information about the relationships between entries. Graph theory is the study of graphs, which are mathematical structures used to model pairwise relations between objects. A "graph" in this context is made up of "vertices" or "nodes" and lines called edges that connect them. A node/vertex represents a patient, provider, resource, etc., and an edge shows a connection between two or more nodes, for example. A graph may be undirected, meaning that there is no distinction between the two vertices associated with each edge, or its edges may be directed from one vertex to another. A directed graph may be unidirectional and/or bidirectional edges, for example. Graphs can be used to model many types of relationships and processes in healthcare systems.

Relationships between people in social networks are one example of a relationship graph. The relationships between items and attributes in recommendation engines are another example. As message exchanges keep flowing through the IntelliLink service bus 502, the graph database is dynamically updated to track relationships and connections within the healthcare ecosystem. The graph can also be periodically updated with reference information such as information from the National Provider Registry, medical reference information, code sets, geographic information, etc.

Graphs can easily be updated with additional data and additional relationships for modeling and analysis, in contrast to traditional analytics. Graph analytics can be used to identify clusters or communities of data points, connections between data points, and/or pattern of relationship(s), for example. In certain examples, graph analytics can be used in at least three distinct areas to help improve the connections in the healthcare ecosystem: connection optimization, usage analytics, and business-to-business (B2B) analytics.

For example, graph analytics can be used to improve connections in the healthcare ecosystem to discover key influencers in healthcare ecosystem by modeling the relationships between patients, providers, visits and readmissions. These relationships can be organized as a graph. Graph analytics can be used to improve connections in the healthcare ecosystem to discover in-efficiencies in electronic data exchanges or lack thereof between patients, healthcare providers and specialist to facilitate traffic optimization, for example. Graph analytics can be used to improve connections in the healthcare ecosystem to discover patient movements and healthcare use patterns to detect cost savings and patient satisfaction improvement opportunities, for example. Graph analytics can be used to discover where there are popular routes between referring providers and specialists, for example. Graph analytics can be used to discover opportunities for healthcare providers to expand their referral networks, for example.

A connection optimizer is a decision support system component that can determine optimum or improved routing information and paths for connections to be established within the ecosystem. The connection optimizer is also used to optimize or improve the routes when provisioning new interfaces and systems in the healthcare exchange ecosystem. For example, the connection optimizer can resolve for an optimum specialist to which a patient should be referred given patient's preferences, date/time, location, cost, treatment options, etc. The connection optimizer can resolve for an optimal date/time to schedule a procedure to avoid bottlenecks, for example. The connection optimizer can resolve for a diagnostics lab, specialist, hospital etc., to which an order should be sent to next to load-balance the request and avoid bottlenecks, for example. The connection optimizer can resolve for patterns of orders that are most likely to result in rejected insurance claims, for example. The connection optimizer can resolve for data sharing agreements which should be established between partners in the ecosystem to improve patient care, for example. Additionally, the connection optimizer can be used to reduce or minimize network costs, optimize performance, and reduce churn in the referral network, reduce patient movements, reduce hospital readmission, etc.

Usage analytics can provide business intelligence regarding complex interactions between users and their healthcare system. Usage analytics tracks a number of users, system configuration, application usage data, etc. In certain examples, usage analytics provide information for a service provider regarding behavior of users of the system that can be used to help drive additional business transactions and increase usage. For example, usage analytics can answer which types of transactions are most common and which value added services are most popular.

B2B analytics provides analytical information about influential doctors, clinics, organizations, etc., and helps discover where there are unmet needs in the healthcare ecosystem. This information can be used for direct marketing to prospective business partners and users of the system, for example.

Certain examples include a machine learning engine to leverage analytics and other information gathered. A machine learning engine (e.g., an R engine) can be trained to discover patterns in message exchanges and taught to detect relationships hidden in large data sets. A predictive capability of the machine learning engine can be used to provide recommendations to the users (providers and patients). In certain examples, machine learning combined with graph analytics provide recommendations and just-in-time contextual information to healthcare providers and users of a healthcare system. For example, a referring healthcare provider can be provided with just-in-time recommendations for specialists and services available within the patient's network. Similarly, recommendations can be provided to the healthcare providers to improve the patient satisfaction by suggesting follow-up communication, for example.

Figure 10A:
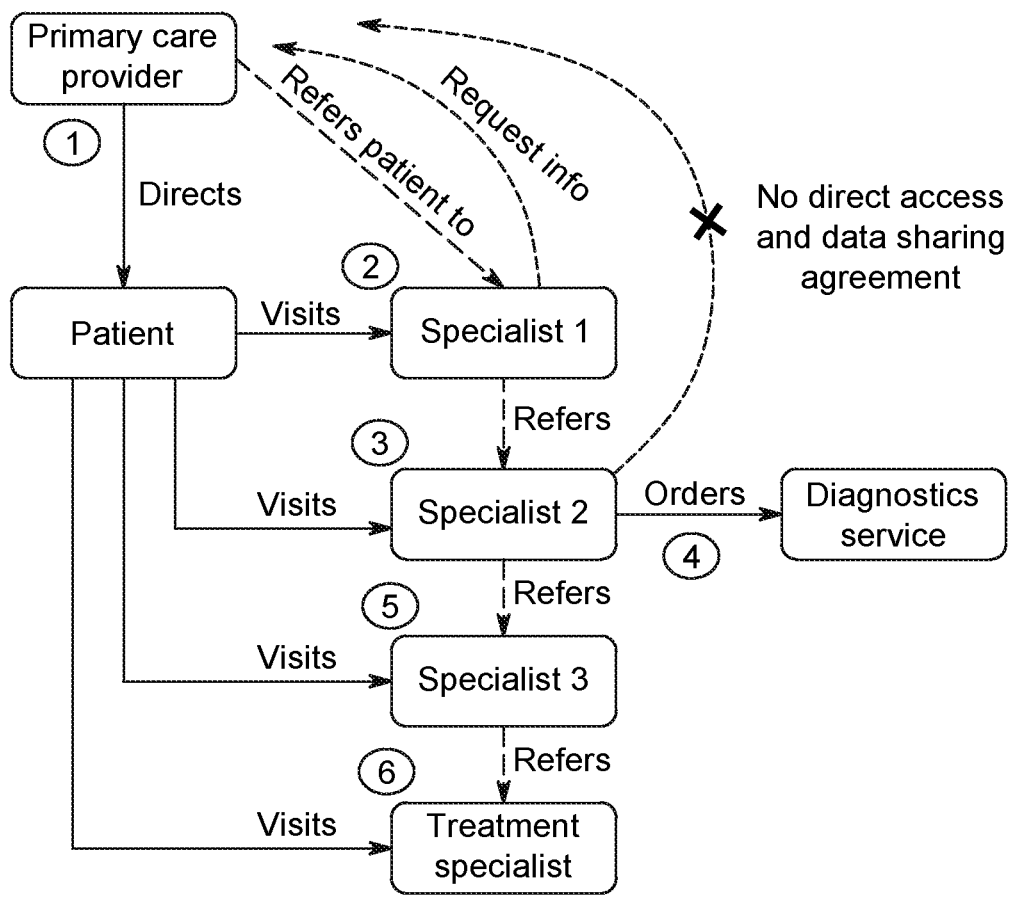
FIGS. 10A-B illustrate an example of intelligent referrals using interface integration.
Figure 10B:
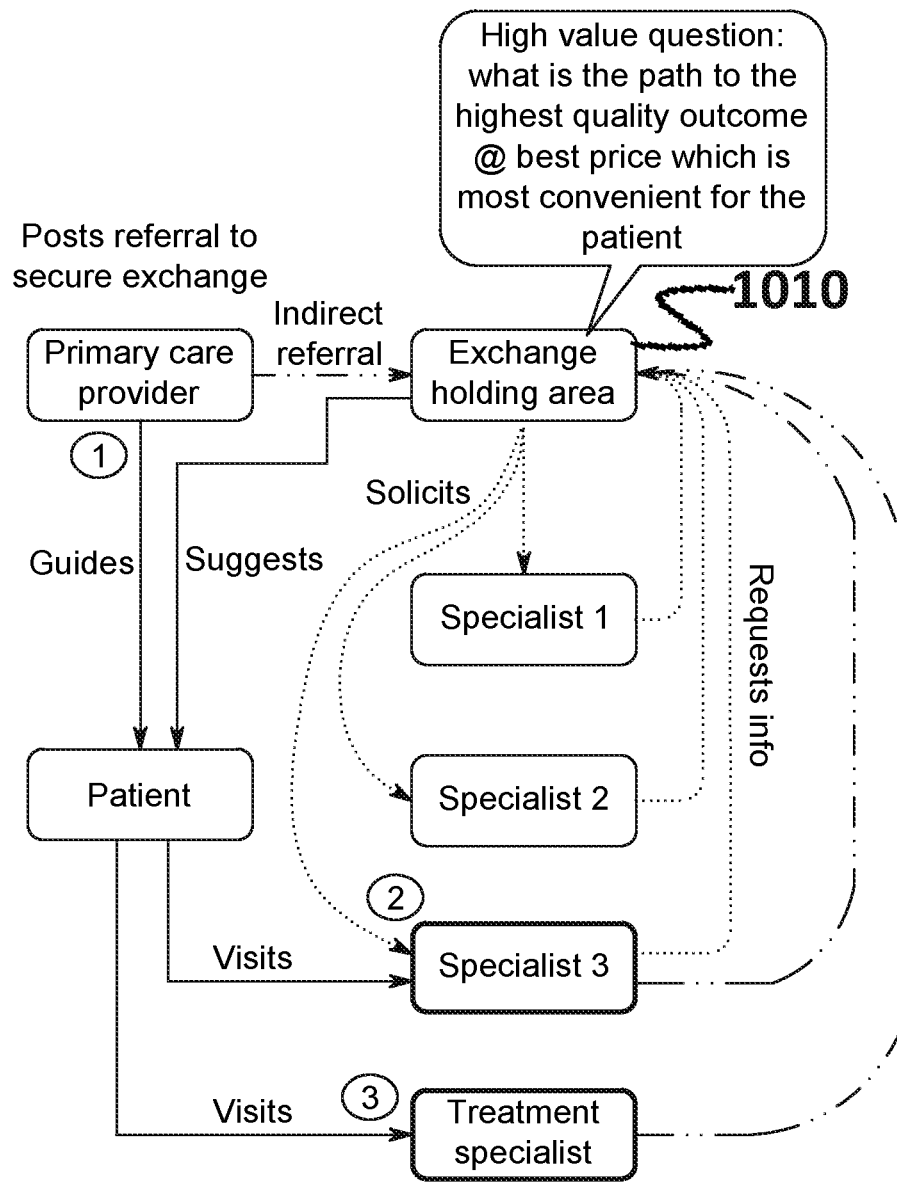

Using the interface integration platform systems and methods, a plurality of solutions can be implemented. In an example, illustrated in FIGS. 10A-B, intelligent referrals can be facilitated. FIG. 10A shows an example of a patient referral by a Primary Care Provider which resulted in unnecessary visits and diagnostics test. FIG. 10B shows an alternative using an intelligent referral to reduce inefficiency and unnecessary action.

As shown in FIG. 10A, the patient ended up making six visits to various specialists before finding the right expert able to treat the patient. For example, as shown in FIG. 10A, the primary care provider refers the patient to a first specialist, who requests information about the patient from the primary care provider and then refers the patient to a second specialist, who has no direct access or data sharing agreement with the primary care physician. As a result, the second specialist orders diagnostic service and refers the patient to a third specialist, who finally refers the patient to a treatment specialist. The lack of data sharing exacerbates the situation which results in severe patient dissatisfaction and the same questions being asked repeatedly of the patient by multiple specialists over multiple visits before treatment can finally be determined and ordered.

As shown in the example of FIG. 10B, the Primary Care Provider makes an indirect referral to the healthcare exchange where the referral record is held in an exchange holding area 1010 until an appropriate specialist is found. The healthcare exchange solicits information from multiple specialists (e.g., specialists 1, 2 and 3) and determines a path to a highest quality outcome at a best price which is most convenient for the patient. The healthcare exchange notifies the patient with identification of one or more suggested specialists in the area that meet the patient's and Primary Care Provider requirements. The patient has the option to request additional information from each specialist which is mediated via the healthcare exchange. The exchange can then suggest a most applicable available specialist to the patient, which leads to a treatment specialist to help the patient. Once the patient has selected the specialist to visit, the graph database is updated which results in the specialist being notified and granted access to view the referral information from the Primary Care Provider.

Figure 11:
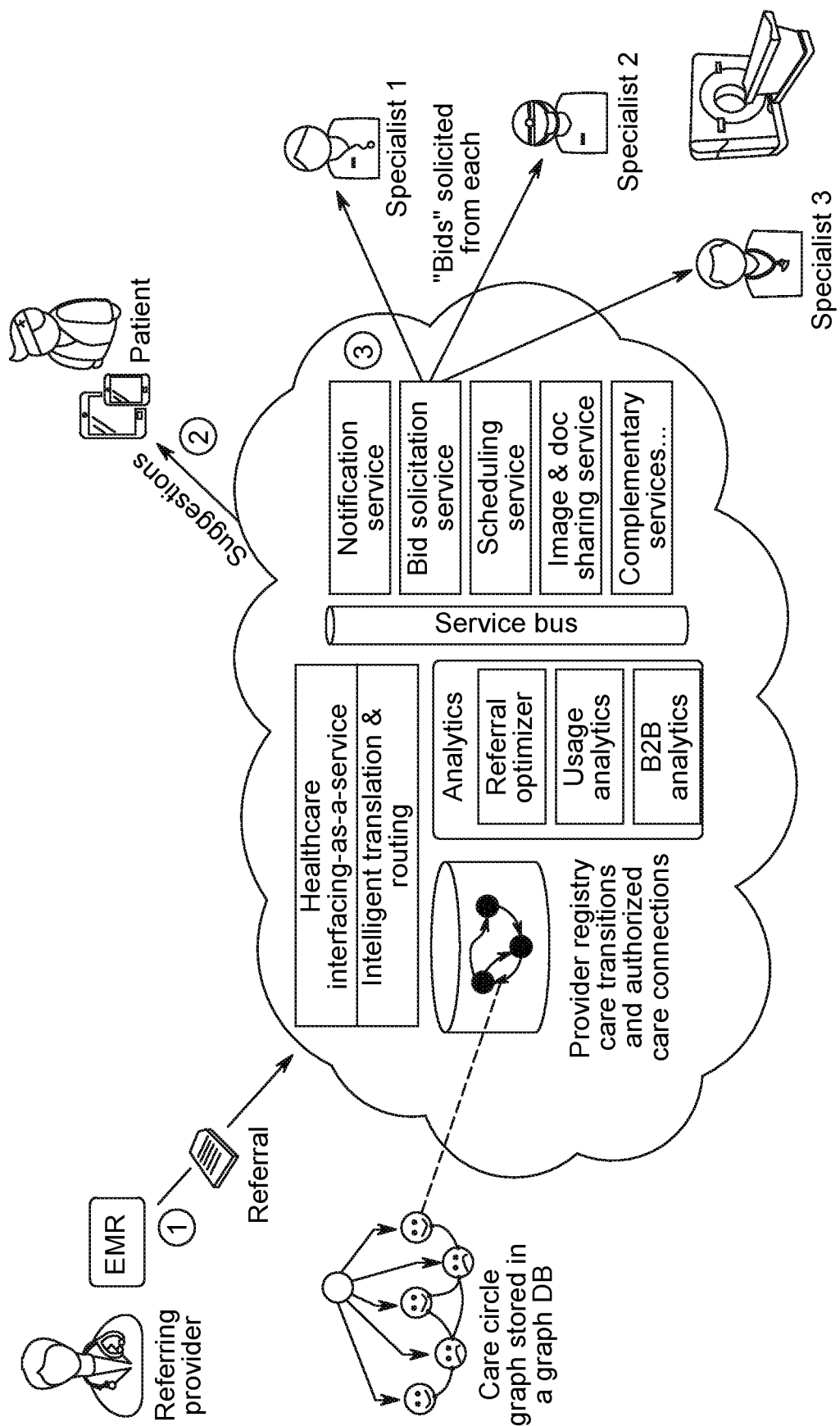
FIG. 11 illustrates an example implementation of "intelligent referrals" with fan outs among specialists.

FIG. 11 illustrates an example implementation of "intelligent referrals" with fan outs among specialists. At point 1 in the example of FIG. 11, a referring provider submits referral documents (e.g., from an EMR and/or other electronic storage) to a healthcare exchange where the referral document(s) are held and stored temporarily. At point 2 in the example of FIG. 11, a patient receives suggestions for multiple specialists within the area. At point 3 in the example of FIG. 11, the patient initiates a bid solicitation via an exchange (e.g., such as the example exchange architecture 400 of FIG. 4) which guides selection of an optimal specialist from the available specialists. The patient can select a specialist who is connected with the referring provider, and the specialist is added to the patient's care circle team. A corresponding graph database is updated. An IaaS, such as the IaaS described in relation to FIGS. 4, 5, 9, etc., can be provided to facilitate interfacing, intelligent translation and routing, analytics (e.g., referral optimizer, usage analytics, B2B analytics, etc.), and a plurality of services (e.g., a notification service, a bid solicitation service, a scheduling service, an image and document sharing service, and/or other complementary services, etc.) via a service bus. A graph database can provide a provider registry including care transitions and authorize care connections for the patient and specialists.

Figure 12:
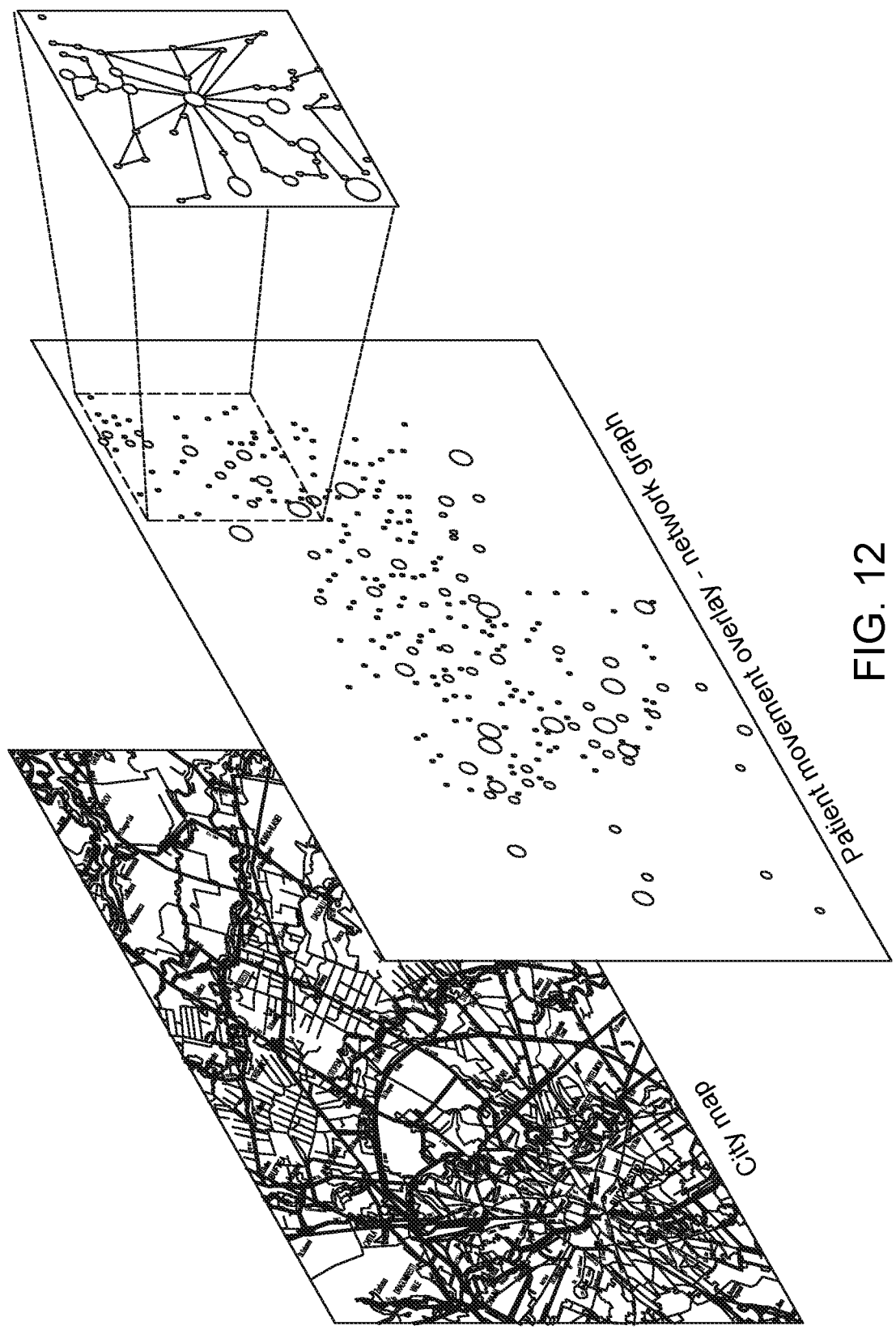
FIG. 12 illustrates an example regarding patient movement and readmission analytics.

FIG. 12 illustrates an example regarding patient movement and readmission analytics. The example of FIG. 12 allows hospitals and clinics to visualize patient movement that results after the patient has been discharged. The solution can be implemented using the graph database of care connections and using graph visualization tools. As shown in FIG. 12, patient movement graphs can be overlaid onto geographic maps to visualize patient movements. A composite view of patient movement can assist planners and hospital quality and compliance officers to investigate hospital readmissions and breakdowns in post-discharge follow-ups.

Figure 13:
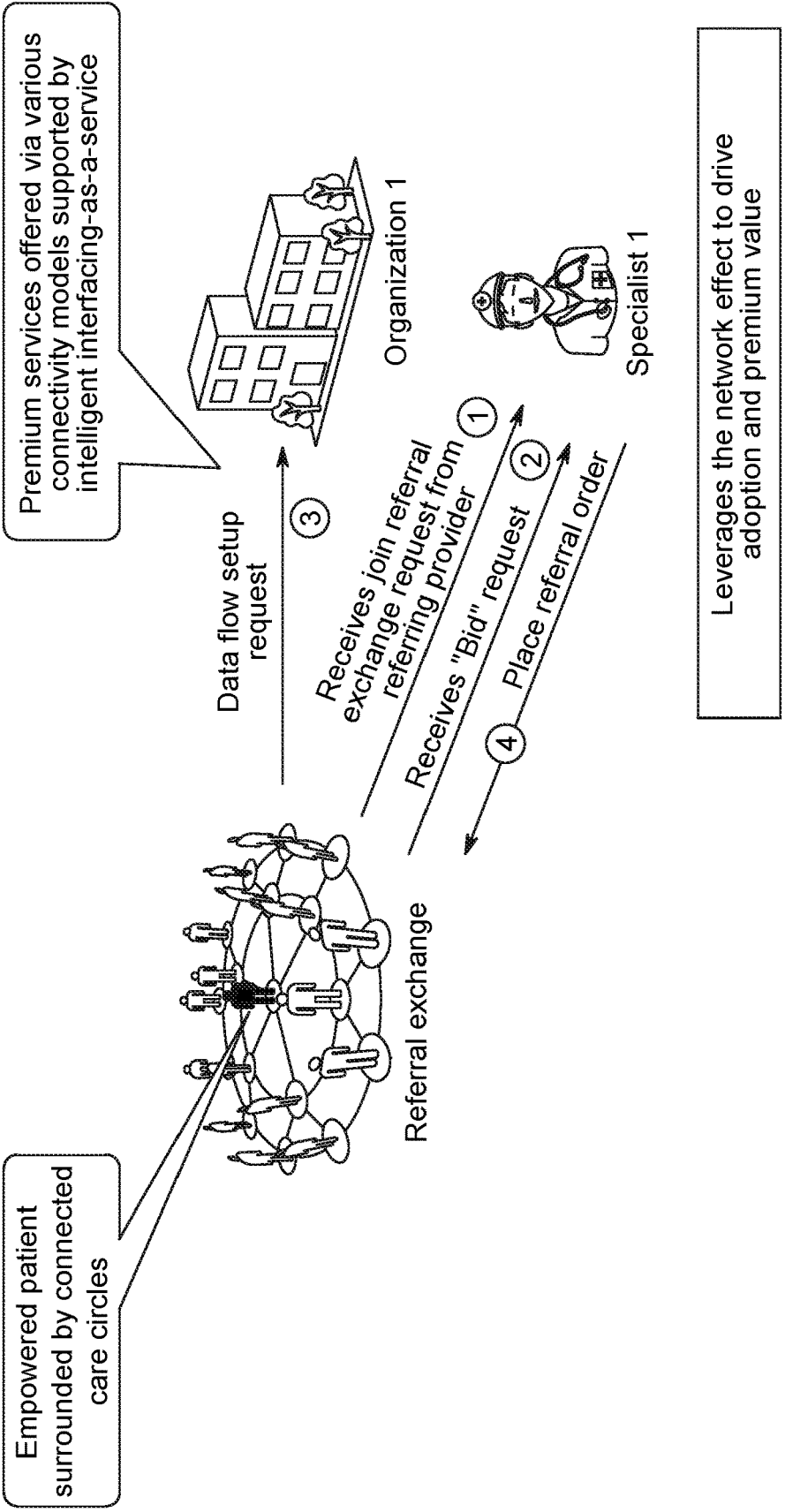
FIG. 13 shows an example of self-forming care teams.

FIG. 13 shows an example of self-forming care teams. In the example of FIG. 13, care providers can send out requests to other clinics, specialists and referrals to join a healthcare social graph (e.g., a referral exchange) which is also stored in a care connection graph database. As shown in FIG. 13, at points 1 and 2, when a specialist receives and accepts a request to join a referral exchange, a corresponding organization also receives, at point 3, a request to setup appropriate data flows with the cloud based integration platform and referral network. Services can be offered via various connectivity models supported by intelligent interfacing-as-a-service, for example. The process of the example of FIG. 13 allows the referral exchange to expand rapidly via a self-service provisioning process for new interfaces and data flows. At point 4 in the example of FIG. 13, a connected specialist can then place a referral order. Thus, the example network and process of FIG. 13 leverages the network effect to drive adoption and premium value in referrals.

Figure 14:
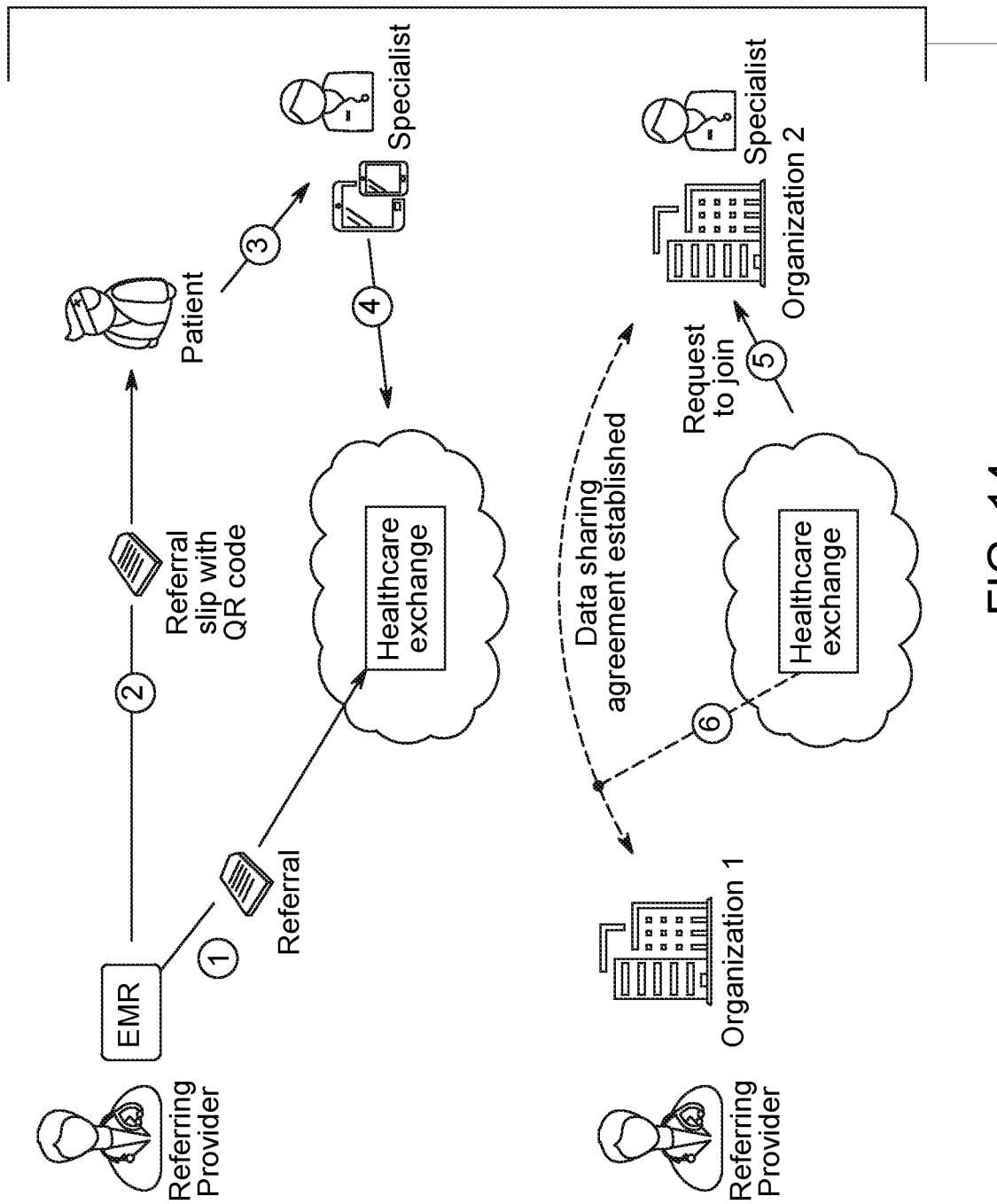
FIG. 14 illustrates an example of movement from indirection to direct connections.

FIG. 14 illustrates an example of movement from indirection to direct connections. FIG. 14 illustrates how disconnected providers get connected via a patient and an associated sequence of events. At point 1 in the example of FIG. 14, a Primary Care Provider makes an indirect referral via a Healthcare Exchange and uploads referral information.

At point 2 in the example of FIG. 14, the patient is given a referral slip with a quick response (QR) code and/or URL to pass on to the specialist. At point 3 in the example of FIG. 14, the patient visits the specialist and hands over the referral slip. At point 4 in the example of FIG. 14, the specialist scans the code via his or her mobile device and gets directed to the Healthcare Exchange portal from where the referral information can be downloaded. At point 5 in the example of FIG. 14, at a later point in time, the Healthcare Exchange system sends the specialist a request for his organization to join the exchange. At point 6 in the example of FIG. 14, a data sharing agreement is established between the Primary Care Provider and the Specialist. The data sharing agreement between the two parties is tracked in the graph database to enable future direct exchanges between the two parties.

Certain examples leverage document data exchanges. A clinical document format for data exchange can use the Consolidated Clinical Document Architecture (CCDA). CCDA represents the result of harmonization efforts from Health Level 7 (HL7), Integrating the Health Enterprise (IHE), Health Information Technology Standards Panel (HITSP), components from the IHE Patient Care Coordination (PCC) and Continuity of Care (CCD). The Consolidated CDA format can be used to cover the following structured clinical documents: Continuity of Care Document (CCD), Discharge Summary, Consultation Notes, Digital Imaging and Communications in Medicine (DICOM) Diagnostic Imaging reports, History and Physical, Operative Note, Progress Note and Procedure Note. The CCDA mandates specific content for each type of the fore-mentioned documents, embodied within sectional clinical data elements. The sectional data is required to be codified with support required for 38 unique Vocabularies including SNOMED-CT and LOINC.

In certain examples, a hospital and/or outpatient electronic health record (EHR) solution can capture, create and transmit the CCD to a Document Registry and Repository (for example could be based on XDS) following every hospital encounter.

In certain examples, the CCD is generated through an XSLT (stylesheet) based transformation service that maps a database-generated proprietary GXML clinical content structure into the CCDA data model. Pursuant to the Vocabulary requirements prescribed by CCDA, a lookup service is used to lookup Vocabulary from a Lexicon Mapping table cross-mapped against CE master concept data and stored within the CE database. Lexicons supporting RxNorm, LOINC, UCUM and SNOMED-CT terminology would have been loaded into the Lexicon Mapping Table using generic loader tools that support loading the respective terminologies from the United States Metathesaurus or any other terminology knowledge base. The vocabulary lookup service will runtime-bind the lexicon code lookup call to happen during the execution of the stylesheet transformation using the Apache Xalan-Java XSLT processor framework (from the Apache Open Source Consortium) that allows to augment the functionality of XSLT with calls to a procedural language using Java-based extension functions. Extensions written in Java are directly supported by Xalan-Java. For the lookup of lexicon code mappings stored within the Lexicon mapping table, use of a Xalan-Java extension function is involved. The basic pattern is as follows: the stylesheet involved in transformation would use an extension function to pass an input string as an argument (containing the medication name contained within the XML source, for example) to the Vocabulary Lookup framework which then lookups the vocabulary code via a DB lookup (JDBC/Hibernate) call. The result set of the query is passed back to the extension function which then plugs the result back into the runtime XSLT processing context. Once a valid formatted CCDA is created it can then be routed to a Document Registry and Repository (DRR) via the IntelliLink Cloud-based Integration solution.

In certain examples, the IntelliLink platform receives a message exchange request from the source system, such as a hospital or ambulatory or specialty clinic, which is sending a message payload (e.g., a Continuity of Care Document CCD conformant to the CCDA specification) to a Health Information Exchange (HIE). In an example, the message payload can include a wrapped Lab Order to be exported in a standard HL7 electronic format to lab service providers. Batch export of immunization information to an immunization registry can also be similarly facilitated. The appropriate messages are generated within the source system and then wrapped within a canonical message format. In an example, an industry-standard interface engine (such as Mirth Connect, Cloverleaf, Iguana, Intersystems Ensemble, Oracle SOA Suite, etc.) can be used on-site to create and securely transmit the message payload from the source system either in transactional or batch-mode onto the IntelliLink message acquisition channel. The on-site interface engine is responsible for receiving, mediating and transforming messages from the internal source application onto a canonical message format as dictated by IntelliLink's message acquisition channel. Messages are then securely routed onward to the IntelliLink Bus for subsequent routing to the subscribed interface.

The message payload being sent from the source system(s) is either the CCD or Lab Order that was created in the Clinical Information System/EMR that embodies the source system. A set of re-usable services can de-identify (and re-identify) Protected Health Information (PHI). In an example, patient data that is sent from the source system is first de-identified using an Enterprise Master Patient Index (EMPI) using an Affinity Domain Patient ID for the transaction. In an example, an Enterprise Master Patient Index (EMPI) system can be used to resolve patient identity.

The EMPI evaluates data from disparate systems within the affinity domain, creates an enterprise unique identifier (EUID) for the record and maintains a map between the EUID and all the local identifiers associated with the patient. De-identification of the source system patient ID prior to sending the request and subsequent Re-identification of the local patient ID from the response coming back from the target system involves a Patient Identifier Cross-reference (PIX) Query between the source system (primarily the interface engine plays the role of a PIX Consumer) and the EMPI system (playing the role of PIX Manager). In an embodiment, the PiX Query is routed within an IntelliLink interface created for the same. PIX Query corresponds to Transaction ITI-9 of the IHE IT Infrastructure Technical Framework and involves a request by the Patient Identifier Cross-reference Consumer Actor for a list of patient identifiers that correspond to a patient identifier known by the consumer. The request is received by the Patient Identifier Cross-reference Manager (the EMPI system). The Patient Identifier Cross-reference Manager immediately processes the request and returns a response in the form of a list of corresponding patient identifiers, if any.

Certain examples impact bio-surveillance and infectious disease outbreak management. In certain examples, such as FIG. 9, data stored within Hive 917 is real-time processed and sent to a streaming Complex Event Processing (CEP) engine 918 to continuously process incoming data, analyze patterns and raise events for certain pre-defined patterns in the data (as shown, for example, in FIG. 9). The CEP 918 can be backed by Business Process Management (BPM) or Business Process Execution Language (BPEL) engine 919 (such as Activiti or any other BPMN2 compliant process engine) to define processes and take appropriate actions based on the event raised. A real time Business Activity Monitor (BAM) dashboard 921 provides immediate insight and generates actions.

A use case for using smart event-detection can include for Public Health Surveillance and Bio-Surveillance for outbreak management. The generated action creates a message and payload for submission of the detected syndromic event to a Public Health Surveillance database. The event-detection algorithms can be based off Laboratory data, Clinical Encounter (Summary of Care) data and non-clinical data that is then sent to various National, State and Local Disease Surveillance systems.

The CDC National Notifiable Disease Surveillance System (NNDSS) requires reporting off laboratory and clinical data on nationally defined list of communicable diseases. Similarly, various State and Local Disease Surveillance Systems exist for syndromic data from clinical and non-clinical sources to detect a public health threat event. Post-Meaningful Use, Public Health Surveillance has mainly focused on syndromic surveillance with a primary focus on event detection based on laboratory, clinical encounter data and non-clinical data.

Data to back up the smart event detection algorithms involves the Consolidated CDA (CCDA): facility demographics including contact data for report and sender data, patient demographics, laboratory and radiology orders/results, vital signs (such as heart rate, respiratory, blood pressure, height and weight), Observation, symptoms and clinical findings, Triage notes, Pregnancy status, severity of illness (ventilated/intubated indicators). Dataset submission requirements are mostly the same as before as specified in the Biosurveillance Minimum dataset and transmitted using HL7 V2.5.1, for example.

A valid action upon detection of syndromic evidence of a disease outbreak or a communicable disease is creation of a message payload that then needs to be translated into an HL7 2.5.x structure based upon the HITSP defined format and sent outbound to the CDC or any State or Local Surveillance system or registry. The workflow process creates the biosurveillance dataset payload that is then routed onward to a pre-defined CDC (or any other third party surveillance system) IntelliLink interface that is then delegated the responsibility of transforming to the correct message protocol and routing the message onward to the target system.

Figure 15A:
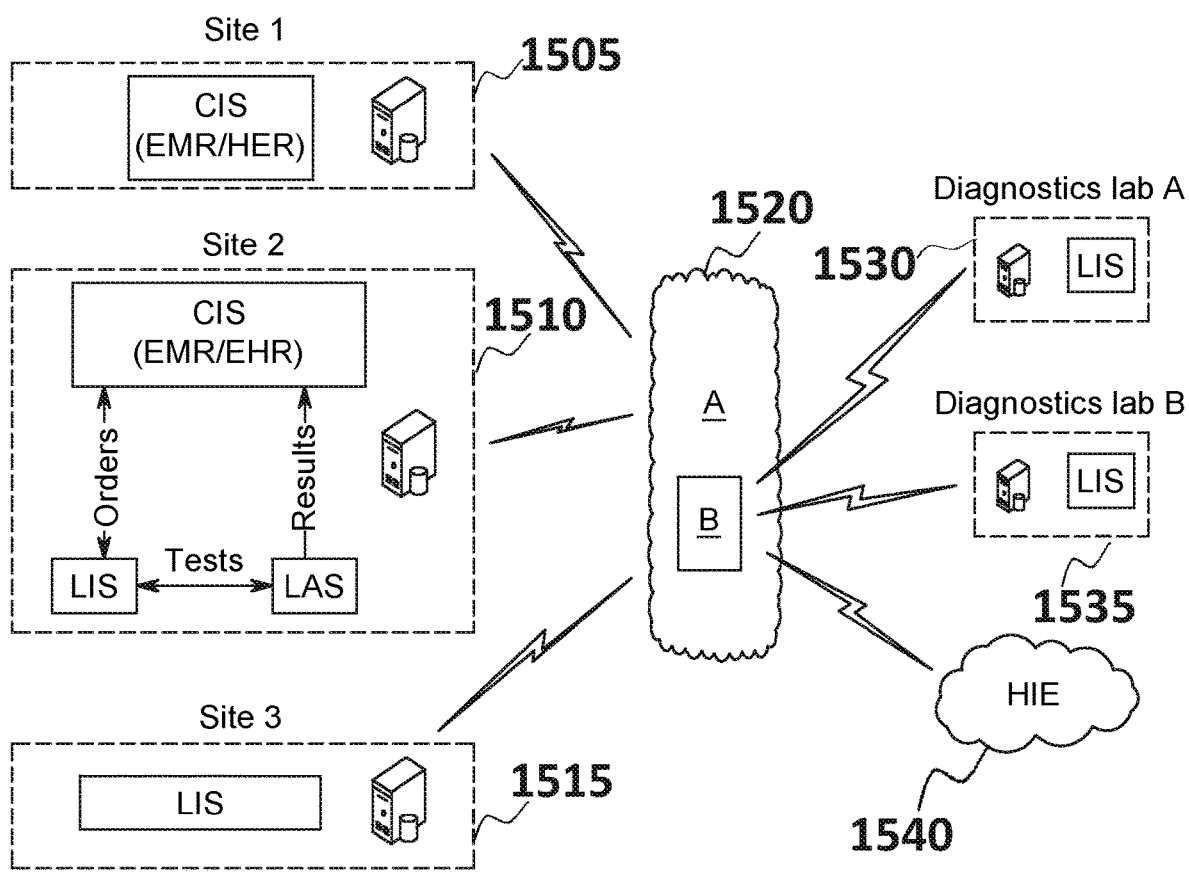
FIGS. 15A-15B illustrate an example schematic of an Interface-as-a-Service realization of a Cloud-deployed laboratory hub.
Figure 15B:
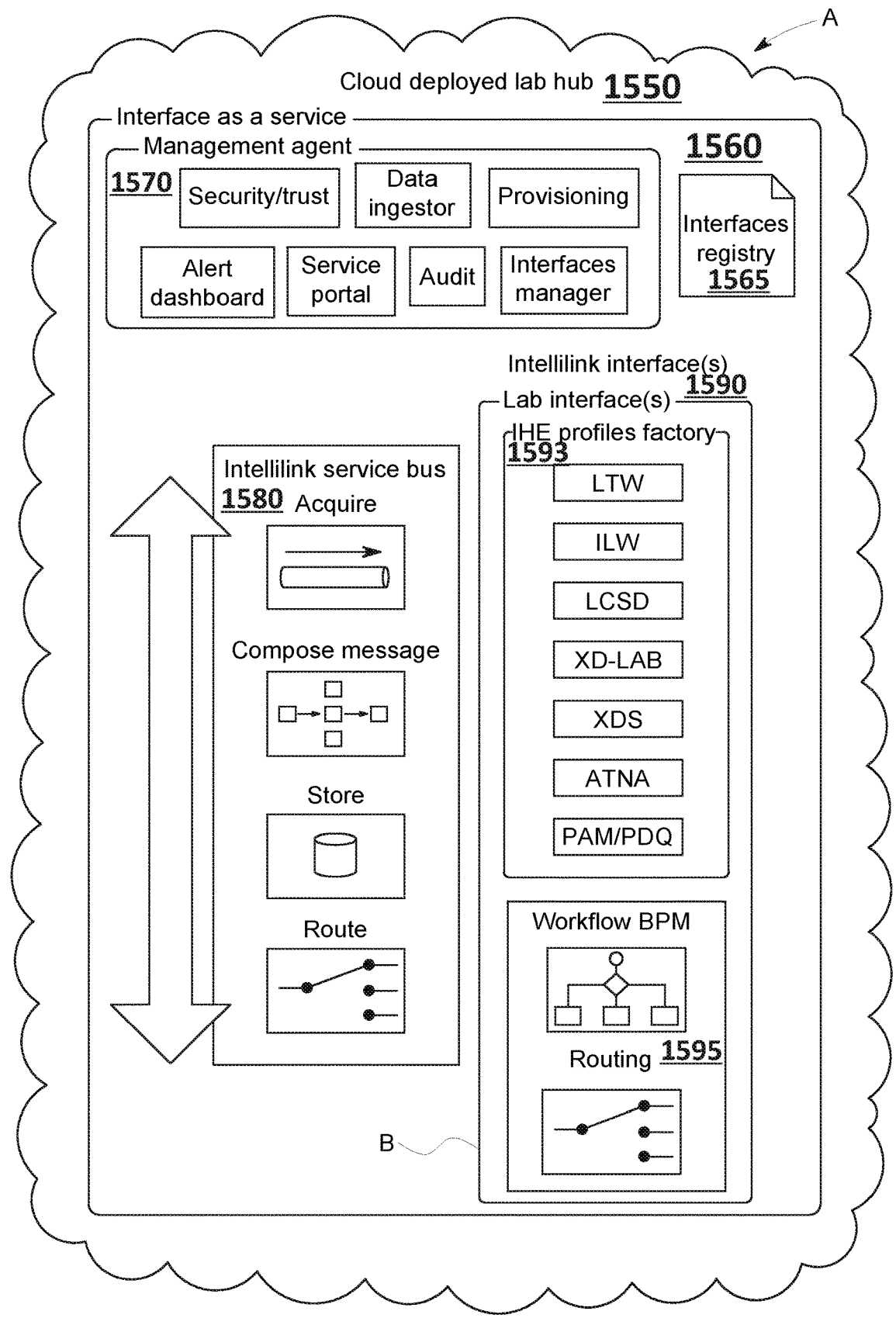

FIGS. 15A-15B illustrate an example schematic of an Interface-as-a-Service realization of a Cloud-deployed laboratory hub. Standards such as HL7 and IHE can be used to realize a cloud-deployed hub by providing standards-based connectivity (e.g., supporting various customer deployments) between Clinical Information Systems (CIS), internal and/or external Laboratory Information Systems (LIS) and Laboratory Automation Systems (LAS). An example of a CIS can be GE's Centricity® Enterprise EHR solution, designed mainly for Hospitals and Medical Centers, or GE's Centricity® Practice Solution designed for large practices and clinics.

IHE provides various Laboratory Profiles addressing information sharing and workflow related to in-vitro diagnostic testing in clinical laboratories. For example, the IHE LTW (Laboratory Testing Workflow) profile integrates the ordering, scheduling, processing and result reporting activities associated with diagnostic tests performed by clinical laboratories in healthcare institutions. The LTW integration profile encompasses the various workflows and actions between the CIS, LIS and LAS (covering Order Placing, Order Filling, Automation manager to Order Results reporting and tracking). The profile leverages IT infrastructure profiles PAM/PDQ for up to date patient and encounter data and the ATNA profile for auditing and security. In an embodiment, an on-premises deployment of a CIS needing to place a Lab Order with an external LIS could send the lab order (wrappering the Lab Order details and communicating the wrapped payload) to a defined IntelliLink interface (e.g., utilizing a Cloud-based Lab Hub infrastructure) that provides a componentized factory implementation of the requisite LTW profile transforming the wrapped Lab Order details into LTW and communicate with the target recipient LIS. The target LIS, playing the role of the Order Filler in this workflow, upon fulfillment of the order, utilizes the IntelliLink infrastructure to route the Results report back to the Order Placer actor CIS. On-premises messaging (either within the CIS or the LIS) occurs through an HL7 Interface engines or gateways.

In certain examples, the interface engine or gateway includes an internal implementation of factory LTW profiles (or ILW or any of the IHE Laboratory Profiles) and creates and sends the Lab Order to the IntelliLink Cloud hub in a wrapped payload created using that profile. In this case, the subscribing IntelliLink interface unwraps and forwards the request on to the target recipient without need for any factory profile transformation(s). The IHE Inter Laboratory Workflow (ILW) profile supports the exchange of test orders and results between two laboratories for the embodiment when the messaging is to happen between two (or several) different LIS's using the same Cloud-based Lab Hub infrastructure. One laboratory is the requester; its LIS implements the new Actor "Requester" that will place test sub-orders to the second laboratory, referred to as the subcontracting laboratory. The LIS of this second laboratory implements the new Actor "Subcontractor" that will fulfill the sub-orders and send the results back to the Requestor Actor. The Laboratory Code Sets Distribution (LCSD) profile enables establishing, maintaining and sharing of common nomenclatures among systems involved in laboratory workflows. The system owning a laboratory code set—the Code Set Master Actor—sends the whole code set to any Code Set Consumer Actor, each time an update on this code set is needed. In an embodiment, a lightweight workflow and Business Process Management platform (BPM), in an embodiment implemented with Activiti BPMN2 process engine, would be required to maintain the state of the execution sequence and determine the next processing step(s). The afore-mentioned Laboratory integration profiles define transactions all of which are based upon HL7 2.5 or 2.5.1 message standard. Each transaction includes a subset of message structures (based on OML, ORU, ORL and OUL) and specifies a set of constraints applying to each message structure.

As shown in the example of FIG. 15A, multiple locations (e.g., Site 1 1505, Site 2 1510, Site 3 1515, etc.) interface with one or more diagnostic labs (e.g., Diagnostics lab A 1530, Diagnostics lab B 1535, etc.) and an HIE 1540 via a cloud-based hub 1520 (including components A and B). As further illustrated in the example of FIG. 15B, a cloud-deployed laboratory hub A 1550 includes an interface as a service 1560 providing a management agent 1570, a service bus 1580, and one or more interfaces 1590 such as lab interface(s) B. While the management agent 1570 ingests data, provides security, and provisions and manages interfaces in conjunction with an interfaces registry 1565, the service bus 1580 acquires data, composes messages and stores and/or routes messages using the interface(s) 1590 (e.g., lab interface(s) B). The lab interface(s) B of the example of FIG. 15B include one or more IHE profiles in an IHE profiles factory 1593 as well as workflow business process management (BPM) and routing 1595, for example.

Figure 16A:
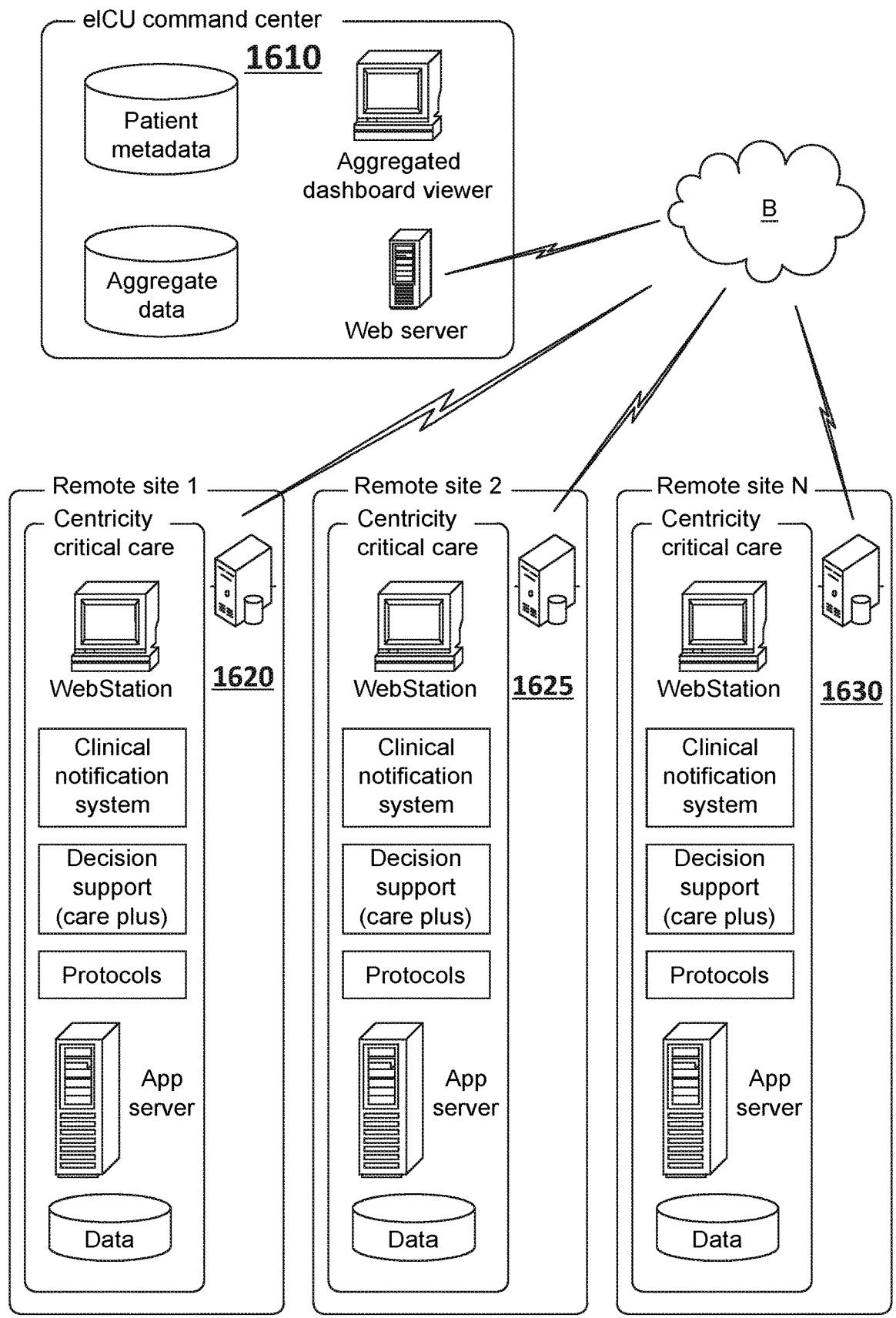
FIGS. 16A-16B illustrate a schematic of an Interface-as-a-Service realization of a tele-ICU solution.
Figure 16B:
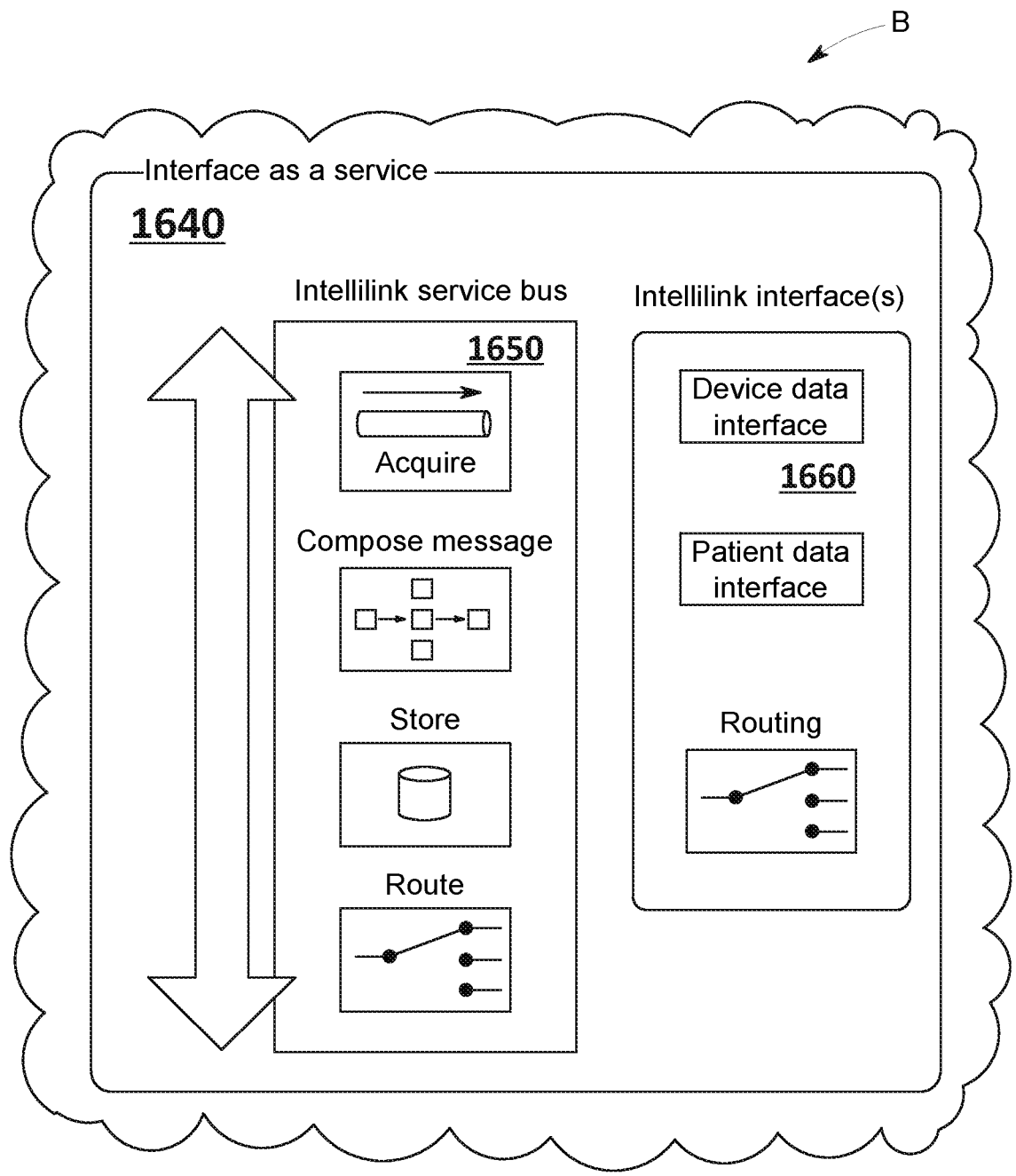

FIGS. 16A-16B illustrate a schematic of an Interface-as-a-Service realization of a tele-ICU solution. The tele-ICU solution can be powered by GE's High-Acuity Care Solutions (e.g., Centricity® Critical Care), for example, and enables a remote hospital to provide advanced consultation, care and monitoring to their critically ill patients without having to transfer them to super-specialty hospitals. Remote ICU monitoring technology that tele-ICU enables allows an intensivist at the command center to monitor real-time parameters of critically ill patients from remote ICUs/Hospitals on a 24/7 basis. The tele-ICU solution assists in timely treatment and monitoring of patients in collaboration with local physicians over audio/video capability that, in an example, is provided along with the solution.

Certain examples provide a Decision Support Module (e.g., GE's Care Plus) interface with an embedded state-of-the-art rules based engine that allows clinical parameters to be tracked and used to generate clinical notifications in an automated workflow. A Medication Interaction module allows predefined protocol support for dosages and integrated with the decision support system assists in raising alerts/events in cases of incorrect care decisions. A Clinical Notification System module (CNS) compares a huge amount of data collected against user-defined rules, identifies potentially relevant clinical events and generates messages in an XML payload that can then be routed and delivered to the command center. A GE or non-GE commercial HL7 interface engine could be used at each remote site to create an HL7 message transport format from the generated XML payload, perform translation services from other proprietary formats and transmit the HL7 to the cloud-based "Interface-as-a-Service". Device and Patient Data IntelliLink interfaces are used to capture, parse, aggregate and cache the content specific to device or patient data streaming from each remote site. The cached data is then periodically sent to a web-based UI application at the command center that generates dashboards and provides aggregated views on actionable information on data across all the remote hospital sites.

In certain examples, cached data from each remote site is sent to a RESTful service running on a web server at the command site which then aggregates the data and pushes it to an HTML5 viewer application using an implementation of Websocket technology. Websockets provides a standardized HTML5 way for the server to send content to the browser without being solicited by the client, and allowing for messages to be passed back and forth while keeping the connection open. In this way, a two-way full-duplex ongoing conversation can take place between a browser and the server. The centralized dashboard console provides aggregated information convergence on patients across all the remote sites to intensivists and clinicians sitting at the command center for pro-active and consultative care. For example, smart alerts built into GE's Centricity systems can flag trends in patient's condition like picking up a spike in a white blood cell count, the start of a low grade fever, etc. The alerts or events raised would be picked up by the Clinical Notification Service that generates the message which is HL7 transformed and sent via the interface engine to the deployed IntelliLink interface and thereon for display to the command center dashboard. When an Intensivist at the tele-ICU command center puts all those together, they are able to conclude if a serious infection is setting in, thereby helping in timely intervention to improve patient outcomes. In an example, the aggregated patient/device data is stored in persistent storage at the command center to re-create the dashboard user interface in case of a transient user interface application outage.

For example, as shown in FIG. 16A, an eICU command center 1610 communicates via an Interface-as-a-service B with one or more remote sites 1620, 1625, 1630. The command center 1610 includes patient metadata, aggregate data, an aggregated dashboard viewer, and a Web server, for example. The remote sites 1620, 1625, 1630 include, in the example of FIG. 16A, Centricity® critical care centers including a Web station, clinical notification system, decision support, one or more protocols, an application service, and associated data.

As shown in the example of FIG. 16B, the eICU command center 1610 communicates with the remote site(s) 1620, 1625, 1630 via an Interface as a service (IaaS) 1640 (e.g., offered via "cloud" B). The IaaS 1640 includes an Intellink service bus 1650 to acquire data, compose message(s), store data, and route messages via one or more Intellink interface(s) 1660. The interface(s) 1660 include one or more device data interfaces, patient data interfaces, and routing infrastructure/information, for example, to enable the command center 1610 to interface with one or more of the remote sites 1620, 1625, 1630 in the example of FIGS. 16A-16B.

IV. Example Computing Device and Computer/Machine Readable Instructions

In certain examples, machine readable instructions can be used to implement the example systems and methods disclosed and described herein. In these examples, the machine readable instructions comprise a program for execution by a processor such as the processor 1712 shown in the example processor platform 1700 discussed below in connection with FIG. 17. The program can be embodied in software stored on a tangible computer readable storage medium such as a CD-ROM, a floppy disk, a hard drive, a digital versatile disk (DVD), a BLU-RAY™ disk, or a memory associated with the processor 1712, but the entire program and/or parts thereof could alternatively be executed by a device other than the processor 1712 and/or embodied in firmware or dedicated hardware. Further, although the example program is described with reference to the flow diagrams and schematics above, many other methods of implementing the example systems and methods can alternatively be used. For example, the order of execution of the blocks can be changed, and/or some of the blocks described can be changed, eliminated, or combined.

As mentioned above, the example processes disclosed above can be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

The subject matter of this description may be implemented as stand-alone system or for execution as an application capable of execution by one or more computing devices. The application (e.g., webpage, downloadable applet or other mobile executable) can generate the various displays or graphic/visual representations described herein as graphic user interfaces (GUIs) or other visual illustrations, which may be generated as webpages or the like, in a manner to facilitate interfacing (receiving input/instructions, generating graphic illustrations) with users via the computing device(s).

Memory and processor as referred to herein can be stand-alone or integrally constructed as part of various programmable devices, including for example a desktop computer or laptop computer hard-drive, field-programmable gate arrays (FPGAs), application-specific integrated circuits (ASICs), application-specific standard products (ASSPs), system-on-a-chip systems (SOCs), programmable logic devices (PLDs), etc. or the like or as part of a Computing Device, and any combination thereof operable to execute the instructions associated with implementing the method of the subject matter described herein.

Computing device as referenced herein can include: a mobile telephone; a computer such as a desktop or laptop type; a Personal Digital Assistant (PDA) or mobile phone; a notebook, tablet or other mobile computing device; or the like and any combination thereof.

Computer readable storage medium or computer program product as referenced herein is tangible (and alternatively as non-transitory, defined above) and can include volatile and non-volatile, removable and non-removable media for storage of electronic-formatted information such as computer readable program instructions or modules of instructions, data, etc. that may be stand-alone or as part of a computing device. Examples of computer readable storage medium or computer program products can include, but are not limited to, RAM, ROM, EEPROM, Flash memory, CD-ROM, DVD-ROM or other optical storage, magnetic cassettes, magnetic tape, magnetic disk storage or other magnetic storage devices, or any other medium which can be used to store the desired electronic format of information and which can be accessed by the processor or at least a portion of the computing device.

The terms module and component as referenced herein generally represent program code or instructions that causes specified tasks when executed on a processor. The program code can be stored in one or more computer readable mediums.

Network as referenced herein can include, but is not limited to, a wide area network (WAN); a local area network (LAN); the Internet; wired or wireless (e.g., optical, Bluetooth, radio frequency (RF)) network; a cloud-based computing infrastructure of computers, routers, servers, gateways, etc.; or any combination thereof associated therewith that allows the system or portion thereof to communicate with one or more computing devices.

The term user and/or the plural form of this term is used to generally refer to those persons capable of accessing, using, or benefiting from the present disclosure.

Figure 17:
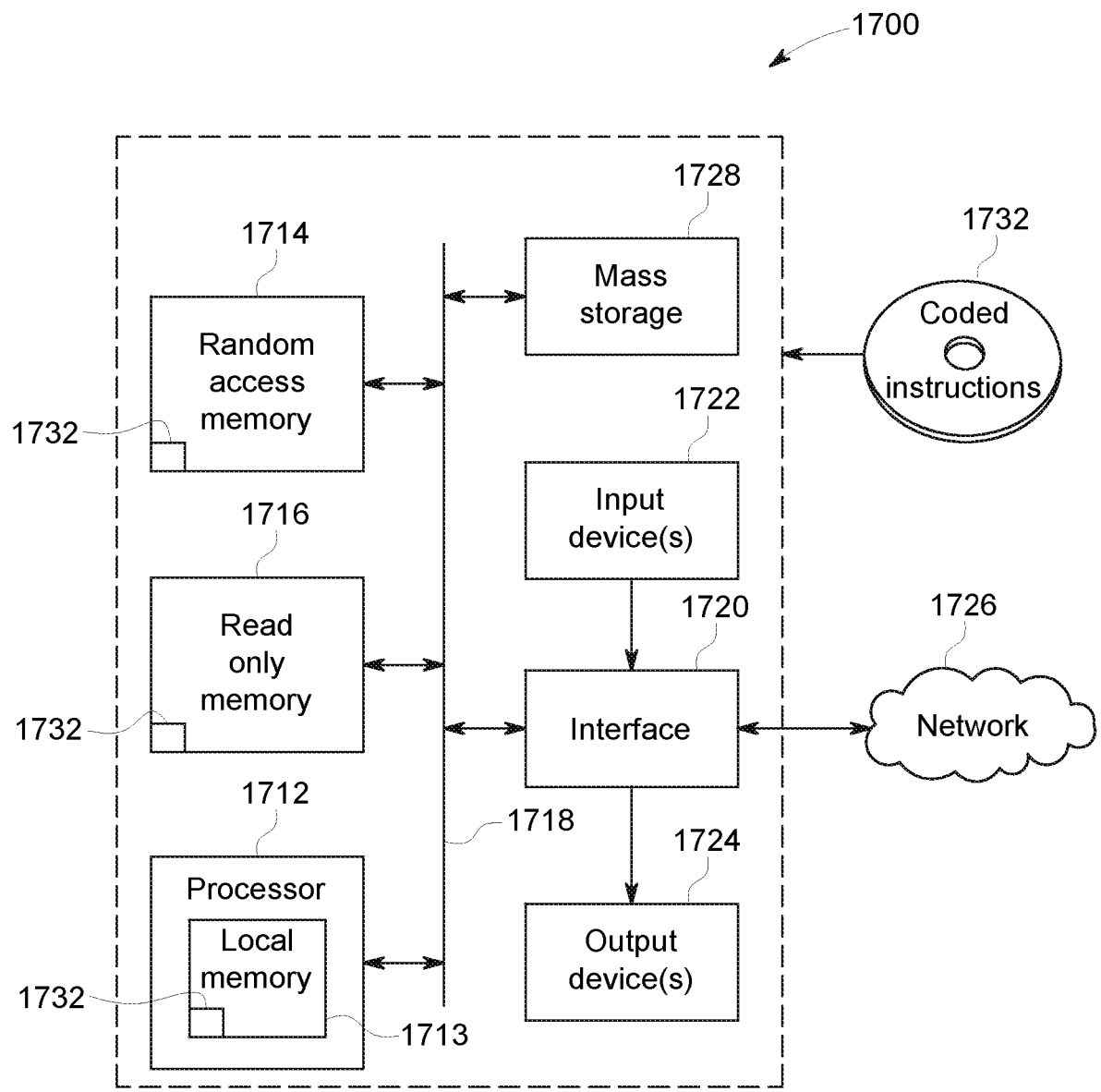
FIG. 17 shows a block diagram of an example processor system that can be used to implement systems and methods described herein.

FIG. 17 is a block diagram of an example processor platform 1700 capable of executing instructions to implement the example systems and methods disclosed and described herein. The processor platform 1700 can be, for example, a server, a personal computer, a mobile device (e.g., a cell phone, a smart phone, a tablet such as an IPAD™) a personal digital assistant (PDA), an Internet appliance, or any other type of computing device.

The processor platform 1700 of the illustrated example includes a processor 1712. The processor 1712 of the illustrated example is hardware. For example, the processor 1712 can be implemented by one or more integrated circuits, logic circuits, microprocessors or controllers from any desired family or manufacturer.

The processor 1712 of the illustrated example includes a local memory 1713 (e.g., a cache). The processor 1712 of the illustrated example is in communication with a main memory including a volatile memory 1714 and a non-volatile memory 1716 via a bus 1718. The volatile memory 1714 can be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1716 can be implemented by flash memory and/or any other desired type of memory device. Access to the main memory 1714, 1716 is controlled by a memory controller.

The processor platform 1700 of the illustrated example also includes an interface circuit 1720. The interface circuit 1720 can be implemented by any type of interface standard, such as an Ethernet interface, a universal serial bus (USB), and/or a PCI express interface.

In the illustrated example, one or more input devices 1722 are connected to the interface circuit 1720. The input device(s) 1722 permit(s) a user to enter data and commands into the processor 1712. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1724 are also connected to the interface circuit 1720 of the illustrated example. The output devices 1724 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). The interface circuit 1720 of the illustrated example, thus, typically includes a graphics driver card, a graphics driver chip or a graphics driver processor.

The interface circuit 1720 of the illustrated example also includes a communication device such as a transmitter, a receiver, a transceiver, a modem and/or network interface card to facilitate exchange of data with external machines (e.g., computing devices of any kind) via a network 1726 (e.g., an Ethernet connection, a digital subscriber line (DSL), a telephone line, coaxial cable, a cellular telephone system, etc.).

The processor platform 1700 of the illustrated example also includes one or more mass storage devices 1728 for storing software and/or data. Examples of such mass storage devices 1728 include floppy disk drives, hard drive disks, compact disk drives, Blu-ray disk drives, RAID systems, and digital versatile disk (DVD) drives.

The coded instructions 1732 can be stored in the mass storage device 1728, in the volatile memory 1714, in the non-volatile memory 1716, and/or on a removable tangible computer readable storage medium such as a CD or DVD.

IV. Conclusion

Thus, certain examples provide a clinical knowledge platform that enables healthcare institutions to improve performance, reduce cost, touch more people, and deliver better quality globally. In certain examples, the clinical knowledge platform enables healthcare delivery organizations to improve performance against their quality targets, resulting in better patient care at a low, appropriate cost.

Certain examples facilitate improved control over data. For example, certain example systems and methods enable care providers to access data from a plurality of target systems based on integrated, dynamic interface provision factory systems/methods. Certain examples facilitate improved control over process. For example, certain example systems and methods provide improved system interface provisioning and dynamic interaction between systems and data. Certain examples facilitate improved control over outcomes via the integrated interface systems and methods. Certain examples leverage information technology infrastructure to standardize and centralize data across an organization. In certain examples, this includes accessing multiple systems from a single location, while allowing greater data consistency across the systems and users.

Certain examples enable value added services through a connected application ecosystem and by making healthcare connectivity a ubiquitous commodity. Interoperability has been one of the healthcare industry's biggest problems for years and lots of companies are profiting from the lack of interoperability. There is a saying that "if you have seen one HL7 interface you have seen one", meaning that no two are alike. This has led to tremendous amount of redundancy and inefficiency in proposed integration solutions.

Thus, certain examples address these challenges, inefficiencies, needs, and failures by removing overlap and redundancy in approach within various Healthcare IT products in solving interoperability problems using a consistent solution across common healthcare integration scenarios. Certain examples provide multiple individual standalone pluggable interfaces as a facade to healthcare IT products inter-connected by a centralized intelligent platform that performs the relevant interactions and orchestration. Certain examples provide creation and provisioning of new interfaces simplified using a standardized governance model and through heavy use of automation. In certain examples, a graph of the connected ecosystem is built up which enables the connections to be optimized and traffic roadblocks to be avoided.

Certain examples provide an agile, flexible, adaptable, "plug-and-play" integration strategy for a variety of healthcare information systems, thereby increasing opportunities for increased customer satisfaction and significant business "wins". For example, providing an Interface-as-a-Service realization within the context of a tele-ICU enables care providers at a remote hospital to provide advanced consultation, care and monitoring to critically ill patients without having to transfer them to super-specialty hospitals. The remote ICU monitoring technology that tele-ICU enables, allows an intensivist at the command center to monitor real-time parameters of critically ill patients from remote ICUs/Hospitals on a 24/7 basis. This technology model (using concepts around Interfacing-as-a-Service as its central thesis) has ramifications in new products that could potentially be launched in the tele-Radiology or the tele-ER space, for example. Certain examples serve as an exchange or broker which solicits who is available for a patient referral while reducing multiple patient visits and centralizing cloud-based exchange, referral, and further action. Analysis, connection, and interfacing can be facilitated at a meta layer to improve relevance while protecting privacy and maintaining compliance.

Technical effects of the subject matter described above can include, but is not limited to, providing systems and methods to build better-connected healthcare ecosystems with improved knowledge of patients, providers, resources, and data. The subject matter disclosed herein provides a technical effect of transforming data, routing data, gaining knowledge of systems and interfaces, and providing analytics to understand how a healthcare ecosystem can be improved and interface(s) created based on patient movement, data exchanged, resources used, etc. Moreover, the system and method of this subject matter described herein can be configured to provide an ability to better understand large volumes of data generated by devices across diverse locations, in a manner that allows such data to be more easily exchanged, sorted, analyzed, acted upon, and learned from to achieve more strategic decision-making, more value from technology spend, improved quality and compliance in delivery of services, better customer or business outcomes, and optimization of operational efficiencies in productivity, maintenance and management of assets (e.g., devices and personnel) within complex workflow environments that may involve resource constraints across diverse locations.

This written description uses examples to disclose the subject matter, and to enable one skilled in the art to make and use the invention. The patentable scope of the subject matter is defined by the following claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An integration platform apparatus to facilitate dynamic definition and configuration of an interface for a tele-intensive care unit (tele-ICU) to provide remote monitoring technology through the interface, the apparatus comprising:
   at least one memory; and
   at least one processor to at least:
      monitor, via a command center, patient parameters for a patient at a first location to identify a trend in a patient condition based on the patient parameters;
      provision, based on a trend in patient condition associated with the patient parameters and patterns generated by graph analytics with machine learning, an interface between the first location and at least one remote system, the interface selected from a plurality of reusable interface and route definitions to translate and exchange data messages between the first location and the at least one remote system; and
      enable exchange of messages between the first location and the at least one remote system via the interface.

2. The apparatus of claim 1, wherein the at least one processor is to trigger an alert with respect to the patient condition based on the exchange of messages.

3. The apparatus of claim 1, wherein the at least one processor is to monitor device parameters at the at least one remote system via the interface.

4. The apparatus of claim 1, wherein the interface is to be provisioned as an interface-as-a-service.

5. The apparatus of claim 1, wherein the patient parameters are to be monitored and displayed via a dashboard at the command center.

6. The apparatus of claim 5, wherein the at least one processor is to implement an interface engine to deploy the interface and to display the patient parameters via the dashboard.

7. The apparatus of claim 1, wherein the integration platform apparatus is a cloud-based apparatus, and wherein the interface is to be provisioned via the cloud.

8. At least one computer readable storage medium including instructions which, when executed, cause at least one processor to at least:
   monitor patient parameters for a patient at a first location to identify a trend in a patient condition based on the patient parameters;
   provision, based on a trend in patient condition associated with the patient parameters and patterns generated by graph analytics with machine learning, an interface between the first location and at least one remote system, the interface selected from a plurality of reusable interface and route definitions to translate and exchange data messages between the first location and the at least one remote system; and
   enable exchange of messages between the first location and the at least one remote system via the interface.

9. The at least one computer readable storage medium of claim 8, wherein the instructions, when executed, cause the at least one processor to trigger an alert with respect to the patient condition based on the exchange of messages.

10. The at least one computer readable storage medium of claim 8, wherein the instructions, when executed, cause the at least one processor to monitor device parameters at the at least one remote system via the interface.

11. The at least one computer readable storage medium of claim 8, wherein the interface is to be provisioned as an interface-as-a-service.

12. The at least one computer readable storage medium of claim 8, wherein the patient parameters are to be monitored and displayed via a dashboard at a command center.

13. The at least one computer readable storage medium of claim 12, wherein the instructions, when executed, cause the at least one processor to implement an interface engine to deploy the interface and to display the patient parameters via the dashboard.

14. The at least one computer readable storage medium of claim 8, wherein the interface is to be provisioned via a cloud-based platform.

15. A computer-implemented method to facilitate dynamic definition and configuration of an interface for a tele-intensive care unit (tele-ICU) to provide remote monitoring technology through the interface, the method comprising:

monitoring, by executing an instruction using at least one processor, patient parameters for a patient at a first location to identify a trend in a patient condition based on the patient parameters;

provisioning, by executing an instruction using the at least one processor and based on a trend in patient condition associated with the patient parameters and patterns generated by graph analytics with machine learning, an interface between the first location and at least one remote system, the interface selected from a plurality of reusable interface and route definitions to translate and exchange data messages between the first location and the at least one remote system; and enabling, by executing an instruction using the at least one processor, exchange of messages between the first location and the at least one remote system via the interface.

16. The method of claim 15, further including triggering an alert with respect to the patient condition based on the exchange of messages.

17. The method of claim 15, further including monitoring device parameters at the at least one remote system via the interface.

18. The method of claim 15, wherein the interface is to be provisioned as an interface-as-a-service.

19. The method of claim 15, wherein the patient parameters are to be monitored and displayed via a dashboard at the command center.

20. The method of claim 19, further including implementing an interface engine to deploy the interface and to display the patient parameters via the dashboard.

* * * * *